(12) United States Patent
Huang et al.

(10) Patent No.: US 8,772,473 B2
(45) Date of Patent: Jul. 8, 2014

(54) MOSTLY NATURAL DNA SEQUENCING BY SYNTHESIS

(75) Inventors: Xiaohua Huang, La Jolla, CA (US); Eric Roller, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 61 days.

(21) Appl. No.: 13/262,369

(22) PCT Filed: Mar. 30, 2010

(86) PCT No.: PCT/US2010/029238
§ 371 (c)(1),
(2), (4) Date: Nov. 11, 2011

(87) PCT Pub. No.: WO2010/117804
PCT Pub. Date: Oct. 14, 2010

(65) Prior Publication Data
US 2012/0046177 A1    Feb. 23, 2012

Related U.S. Application Data

(60) Provisional application No. 61/211,597, filed on Mar. 31, 2009, provisional application No. 61/211,526, filed on Mar. 30, 2009.

(51) Int. Cl.
*C07H 21/00* (2006.01)
(52) U.S. Cl.
USPC ........................................................ 536/25.3
(58) Field of Classification Search
None
See application file for complete search history.

(56) References Cited

U.S. PATENT DOCUMENTS

| 6,087,095 | A | 7/2000 | Rosenthal et al. |
| 6,482,595 | B2 | 11/2002 | Shuber et al. |
| 2002/0055100 | A1 | 5/2002 | Kawashima et al. |
| 2002/0120126 | A1 | 8/2002 | Church et al. |
| 2005/0014175 | A1 * | 1/2005 | Quake ............................... 435/6 |
| 2009/0197257 | A1 | 8/2009 | Harris |

FOREIGN PATENT DOCUMENTS

| WO | WO 01/94546 A2 | 12/2001 |
| WO | WO 2007010263 A2 * | 1/2007 |

OTHER PUBLICATIONS

International Search Report from PCT/US2010/029238, dated Apr. 25, 2011,(5 pages).

* cited by examiner

*Primary Examiner* — Anne Gussow
*Assistant Examiner* — Mindy G Brown
(74) *Attorney, Agent, or Firm* — Kilpatrick Townsend & Stockton LLP

(57) ABSTRACT

The invention provides a new method for DNA sequencing called "natural sequencing by synthesis" (nSBS). According to the method, DNA that includes a desired sequence is synthesized using a dNTP mix with a small percentage of fluorescently-labeled nucleotides. The fluorescent label is cleavable. In contrast to previous methods that utilize 100% labeled nucleic acids, use of a small percentage of labeled nucleic acids minimizes the distortion of the natural structure of the extending DNA strand and the DNA polymerase. Using the disclosed methods with less than 10,000 copies of template DNA and 10% of the nucleotides labeled, long homopolymer stretches up to 20 bases can be sequenced with high accuracy and Q20 (with 99% accuracy) read lengths of up to 1,000 bases can be achieved. A Q20 read length of greater than 100 bases can potentially be achieved, even if the sequencing is performed with 1,000 copies of a template and 10% of the nucleotides labeled.

16 Claims, 9 Drawing Sheets

MOSTLY NATURAL DNA SEQUENCING BY SYNTHESIS

STATEMENT AS TO RIGHTS TO INVENTIONS MADE UNDER FEDERALLY SPONSORED RESEARCH OR DEVELOPMENT

This invention was made with Government support under National Institutes of Health (HG004103). The Government has certain rights in the invention.

CROSS-REFERENCES TO RELATED APPLICATIONS

The present application is the U.S. National Stage entry of International Application No. PCT/US2010/029238, filed Mar. 30, 2010, which claims priority to U.S. Provisional Appl. No. 61/211,526, filed Mar. 30, 2009, and U.S. Provisional Appl. No. 61/211,597, filed Mar. 31, 2009, incorporated herein by reference in their entireties.

BACKGROUND OF THE INVENTION

Several platforms for high throughput DNA sequencing have recently emerged (See Shendure & Ji (2008) *Nat Biotechnol* 26, 1135-45 for a comprehensive recent review). The most noticeable ones include the Roche/454 Genome FLX (Margulies et al. (2005) *Nature* 437, 376-80; Rothberg & Leamon (2008) *Nat Biotechnol* 26, 1117-24), Illumina/Solexa Genome Analyzer (Fedurco et al. (2006) *Nucleic Acids Res.* 34, e22; Turcatti et al. (2008) *Nucleic Acids Res* 36, e25), Helicos Heliscope (Harris, T. D. et al. (2008) *Science* 320, 106-9) and Life Technologies/ABI SOLiD system (Shendure et al. (2005) *Science* 309, 1728-32; Cloonan et al. (2008) *Nat Methods* 5, 613-9; Valouev et al. (2008) *Genome Res* 18, 1051-63). With these streamlined technologies, the cost for genome resequencing has been dramatically reduced. Except for the SOLiD system, which is based on DNA sequencing by ligation, all other platforms are based on the DNA sequencing by synthesis (SBS) method where the DNA sequence is determined by the cyclic addition of nucleotide bases one base type at a time using either natural nucleotides or fluorescently-labeled nucleotides with a reversible terminator.

The Solexa/Illumina system utilizes SBS with reversible terminators to sequence clonal DNA clusters amplified by in situ bridge PCR. All of the nucleotides in this method are fluorescently labeled, and blocked at the 3' hydroxyl group with a reversible termination group. The sequence of the template is interrogated one base at a time by performing cyclic single base extension (i.e., each of the four nucleotide bases in sequence) from a primer. The 3'-OH blocking group and fluorescent label are cleaved before each cycle. Even though the technology is more streamlined, scalable, and has a higher throughput per run, sequence read length is quite limited and accuracy is low. The limited read length is most likely due to the use of a relatively low number of templates (~1,000 copies), highly engineered non-natural DNA polymerases, and non-natural nucleotides having a cleavable fluorescent dye on the base and a reversible terminator on the 3' hydroxyl group. The step-wise incorporation of such sterically hindered non-natural nucleotides is slow and inefficient, even with DNA polymerases engineered to work with these nucleotides. This results in a significant fraction of the templates falling out of synchronization in each cycle. Various strategies can be used to improve read length and accuracy. These include the use of a better combination of DNA polymerase and fluorescently-labeled nucleotides with cleavable terminator to improve incorporation efficiency and a resynchronization step (Wu et al. (2007) *Proc Natl Acad Sci USA* 104, 16462-7).

The Roche/454 platform makes use of natural DNA polymerases and nucleotides. It is based on pioneering pyrosequencing technology (Ronaghi et al. (1998) *Science* 281, 363, 365), where the sequence is determined by detecting the chemiluminescence signal generated by a cascade of enzymes triggered by the pyrophosphates released upon nucleotide incorporation by a DNA polymerase. Since natural DNA polymerases have intrinsically high fidelity and can synthesize long diverse DNA sequences, including homopolymer stretches (a sequence with more than one base of the same type in tandem), long read lengths and high accuracy can be achieved with this technology. Read length has been improved from about 100 bases to more than 400 bases with high accuracy (Rothberg & Leamon (2008) *Nat Biotechnol* 26, 1117-24; Mashayekhi & Ronaghi (2007) *Anal Biochem* 363, 275-87). However, pyrosequencing involves a complex multi-enzyme cascade (polymerase, sulfurylase and luciferase) that is used to generate pyrophosphate and emit a light signal. This results in a reduced detection sensitivity, which in turn necessitates the use of a large number of templates (>1 million) and a large volume of reagents. To limit cross talk due to diffusion, large wells and an expensive high-density CCD camera coupled to an etched fiber optic plate are utilized for real-time signal detection. This limits the scalability and throughput of the system.

Through massive parallelization and miniaturization, the throughput of DNA sequencing has been increased tremendously while the cost of sequencing has been reduced by several orders of magnitude compared to the conventional gel or capillary-based sequencers using the Sanger dideoxy sequencing method. Emerging sequencing platforms seek to increase the throughput and reduce the cost of DNA sequencing even further to give us the so-called $1000 genome sequencing technology (Rothberg, J. M. and Leamon, J. H., *Nat Biotechnol,* 26; 1117-1124 (2008); Schloss, J. A., *Nat Biotechnol,* 26:1113-1115 (2008); Shendure, J. and Ji, H., *Nat Biotechnol,* 26:1135-1145 (2008)).

Despite the recent progress and developments, further improvements are still needed. Sequencing a mammalian-sized genome remains a time-consuming and expensive endeavor, with costs ranging from 1 to 10 million dollars per genome at 7-fold coverage (National Human Genome Research Institute, Revolutionary Genome Sequencing Technologies—The $1000 Genome (R01), available on the World Wide Web at genome.gov/10000368). Applications that require the sequencing of many individual human genomes are not practical without the development of faster and cheaper sequencing technology. The genomic sequences of normal, neoplastic, and malignant cells from a large number of individuals will be needed for comparative genomics and association studies to dissect the genetic basis of cancer, complex traits/diseases, and personalized medicine.

The present invention provides improved methods for sequencing genetic materials, e.g., for medical applications and biomedical research. The disclosed methods can be applied to rapid personalized medicine, genetic diagnosis, pathogen identification, and genome sequencing for any species in the biosphere.

BRIEF SUMMARY OF THE INVENTION

The present invention utilizes the best proven aspects of SBS using natural DNA synthesis with streamlined methods for DNA amplification and high-speed fluorescence imaging. The result is a significantly improved platform for rapid and inexpensive genome re-sequencing and de novo sequencing. The platform is called natural Sequencing By Synthesis (nSBS) Amplified DNA clones can be sequenced in a massively parallel fashion using cyclic SBS. These methods can be applied using primarily unmodified (or natural) DNA polymerases and nucleotide mixtures. A small percentage of non-terminating nucleotides with cleavable fluorescent labels are incorporated along with natural (unlabeled) nucleotides in the nSBS process, so the natural structure of the extending DNA template is maintained and DNA synthesis is not significantly perturbed. The fluorescently-labeled nucleotide incorporation is sparse, and the fluorescent moiety can also be cleaved off after each imaging step.

Accordingly, the invention provides methods of determining a target sequence using nSBS, and in some embodiments, paired end sequencing. For the sake of convenience, DNA sequencing using a DNA polymerase is discussed, though the disclosed methods can be used for sequencing RNA, e.g., using reverse transcriptase and/or RNA polymerase.

In some embodiments, the method comprises the steps of (a) hybridizing a polynucleotide that comprises the target DNA sequence with a primer to form a hybridized template; (b) contacting the hybridized template with a DNA polymerase and a first single nucleotide solution under conditions to allow target DNA-dependent extension from the primer if the appropriate single nucleotide is present, wherein the single nucleotide solution comprises labeled and non-labeled nucleotides; (c) washing to remove unincorporated nucleotides; and (d) determining the presence or absence of an incorporated labeled nucleotide from the single nucleotide solution, thereby determining the target DNA sequence.

In some embodiments, the method further comprises (e) repeating steps (b)-(d) with a second, third, and fourth single nucleotide solution until a signal is detected. In some embodiments, the method further comprises (e) repeating steps (b)-(d) with a second, third, and fourth single nucleotide solution regardless of whether a signal is detected earlier. That is, all four single nucleotide solutions are added iteratively during each "cycle," in order to determine the identity of the nucleotide at each position. In some embodiments, the method further comprises (f) cleaving the label from the incorporated labeled nucleotide, and repeating the steps of the method to generate a longer sequence. In some embodiments, step (f) is repeated more than 10 times, e.g. 20, 50, 100, 200, 300, 400, 500, 1000, or more times, thereby generating additional sequence information for the target DNA. In some embodiments, the method further comprises adding DNA polymerase (if necessary) and unlabeled nucleotides, and synthesizing the remaining DNA strand without detecting the sequence.

In some embodiments, the percentage of labeled nucleotides incorporated into the nascent strand is 20% or less of the total number of nucleotides incorporated. In some embodiments, the percentage of labeled nucleotides incorporated is less than 15, 12, 10, 9, 8, 7, 6, 5, 4, 3, 2, 1% or less of the total number of nucleotides incorporated (though greater than 0%). In some embodiments, the percentage of labeled nucleotides incorporated in the nascent strand is 1-10%, 1-15%, 5-25%, 10-30%, 5-15%, 1-12%, 8-12%, 5-10%, or 5-12%, or about 10%. The percentage of labeled nucleotides in the single nucleotide solution is generally higher than the percentage of labeled nucleotides that are incorporated into the nascent strand by the DNA polymerase. For example, in some embodiments, the percentage of labeled nucleotides in the single nucleotide solution is greater than 10%, e.g., about 20, 30, 40, 50, 60, 70, 80, or 90% of the total number of nucleotides in the solution. In some embodiments, the percentage of labeled nucleotides in the single nucleotide solution is 10-50%, 20-60%, 50-80%, 10-20%, 20-30%, 30-40%, 40-50%, 50-60%, 60-70%, 70-80%, or 80-90%.

In some embodiments, the labeled nucleotides are labeled with a fluorescent, luminescent, or other light-emitting moiety. In some embodiments, the label is attached to the nucleotide via a linker. In some embodiments, the linker is cleavable, e.g., through a photochemical or chemical cleavage reaction. In some embodiments, the label (or linker) is attached to the nucleotide base, or to another site on the nucleotide that does not interfere with elongation of the nascent strand of DNA. In some embodiments, the linker comprises a disulfide or PEG-containing moiety.

In some embodiments, the target DNA is from genomic DNA, e.g., a genomic DNA fragment, e.g., from a human. In some embodiments, the target DNA is from a pathogen, e.g., a bacteria or virus. In some embodiments, DNA polymerase is the only enzyme added to the reaction after step (b).

In some embodiments, the hybridized template is attached to a solid support, e.g., an array surface or a bead. Either the polynucleotide comprising the target DNA or the primer can be attached to the solid support. In some embodiments, the hybridized template is directly attached to the solid support, e.g., via direct interaction with the surface as described herein. In some embodiments, the hybridized template is indirectly attached to the solid support. For example, in some embodiments, the hybridized template, or multiple hybridized templates, is attached to a linear polymer, which is in turn attached to the solid support.

In some embodiments, the solid support comprises multiple (>1) distinct areas (e.g., domains, spots, wells, etc.), wherein each distinct area is attached to a hybridized template. In some embodiments, each distinct area on the solid support contains a hybridized template with a different target DNA sequence. In some embodiments, within each distinct area on the solid support, the target DNA sequence in the hybridized template is the same, i.e., the target DNA in each distinct area is clonal. That is, the target DNA sequence in each hybridized template attached to the distinct area is the same within each distinct area, but different between the distinct areas. In some embodiments, the method of determining target DNA sequence is performed in parallel in more than one distinct area. In some embodiments, each distinct area comprises several target DNA sequences, e.g., attached to a linear polymer or not. In some embodiments, about 10, 20, 50, 100, 200, 500, 1000, 5K, 10K, 20K, 100K or more copies of target DNA are in each distinct area.

In some embodiments, the target DNA sequence is amplified before step (a). In some embodiments, the amplification comprises bridge PCR or a variant thereof. In some embodiments, the amplification comprises rolling circle amplification, or a combination of bridge PCR and rolling circle methods. In some embodiments, the target DNA sequence is more than 100, 200, 500, or 1000 nucleotides (base pairs) in length, e.g., 2000, 5000, 10,000 or more nucleotides.

In some embodiments, the polynucleotide comprising the target DNA sequence comprises adaptor oligonucleotides, e.g., to hybridize to primers for amplification or synthesis or, e.g., for attachment to a solid support. In some embodiments, the primer hybridized in step (a) is a hairpin primer. In some embodiments, the method further comprises paired end sequencing.

The invention further provides methods of paired end sequencing. In some embodiments, the method comprises (a) ligating a hairpin primer to a first polynucleotide comprising the target DNA sequence to form a first ligated template; (b) contacting the first ligated template with a DNA polymerase, and a solution comprising at least a single nucleotide solution under conditions to allow target DNA-dependent extension from the hairpin primer, thereby forming an extended polynucleotide; (c) contacting the extended polynucleotide with a primer complementary to at least a portion of the hairpin primer of step (a) to form a hybridized template; (d) contacting the hybridized template with a DNA polymerase and a solution comprising at least a single nucleotide solution under conditions to allow target DNA-dependent extension from the primer, thereby forming a second polynucleotide comprising a single-stranded portion and a double-stranded portion; (e) ligating a hairpin primer to the second polynucleotide to form a second ligated template; and (f) contacting the second ligated template with a DNA polymerase and a solution comprising at least a single nucleotide solution under conditions to allow target DNA-dependent extension from the hairpin primer, thereby forming a double-stranded polynucleotide, wherein the sequence of the target DNA is detected during at least one of steps (b), (d), and (f), thereby performing paired end sequencing of a target DNA sequence.

In some embodiments of paired end sequencing, the sequence of the target DNA is determined according to the nSBS methods outlined above. In some embodiments, the target DNA sequence is determined during steps (b) and (f).

In some embodiments, the first polynucleotide comprising the target DNA sequence is attached to a solid support, e.g., an array surface or a bead. In some embodiments, the polynucleotide is directly attached to the solid support. In some embodiments, the polynucleotide is indirectly attached to the solid support. For example, in some embodiments, the polynucleotide, or multiple polynucleotides, are attached to a linear polymer, which is in turn attached to the solid support. As explained above, the solid support can comprise multiple distinct areas. In some embodiments, each distinct area comprises several target DNA sequences, e.g., attached to a linear polymer or not. In some embodiments, the target DNA in each distinct area is clonal, i.e., the same within each distinct area. In some embodiments, about 10, 20, 50, 100, 200, 500, 1000, 5K, 10K, 20K, 100K or more copies of target DNA are in each distinct area. In some embodiments, the method comprises a wash step after steps (b), (d), and (f), e.g., to remove unincorporated nucleotides, cleaved label, or other components from the template.

In some embodiments, the paired end sequencing method further comprises determining the length of the target DNA. In some embodiments, the method further comprises determining the length of the unsequenced target DNA (if any). This information can be used to align and assemble genomic sequences comprising multiple target DNA sequences.

BRIEF DESCRIPTION OF THE DRAWINGS

FIG. 2A: A sequencing machine with built-in microfluidics, programmable temperature control and high-speed fluorescence imaging. The image shows only the objective and imaging chamber with flow cells.

FIG. 2B: The cyclic nucleotide-by-nucleotide sequencing process. Each cycle includes four nucleotide flows and each flow entails 3 steps: (1) One of the four types of nucleoside triphosphates is flowed into the reaction chamber. The nucleotide mix contains natural nucleoside triphosphates and a percentage of the same nucleotide labeled with a fluorescent dye molecule via a cleavable linker. If desirable, the DNA polymerase and any other necessary components can be preloaded onto the templates or added into the reaction mix, or both. (2) After a brief washing to remove the reaction mix from the chamber, an imaging step is performed to measure the fluorescence intensity. (3) The fluorescent labels are cleaved off either chemically or photochemically and this is followed by an extensive washing to remove any residual nucleotides to prevent carry-forward extension in subsequent nucleotide flows. Primed templates: DNA templates with a priming site (i.e., a hybridized template). Fluor: fluorescence molecule labeled to the nucleotide via either a chemically or photochemically cleavable linker; x %, y %, z %, and w %: percentage of fluorescently-labeled dATP, dCTP, dGTP and dTTP, respectively, to give f fraction labeled nucleotide incorporation; nA, nC, nG and nT: the number of A, C, G and T bases, respectively, incorporated at the 3'-end of the primer or nascent strand.

FIG. 2C: An example plot of the signals detected over the cyclic nucleotide-by-nucleotide sequencing process and the corresponding base calling.

FIG. 2D: The probability distribution of the number of labeled nucleotides incorporated for various length homopolymers (L=0 to 20) with 1,000 copies of a template (N=1,000) and 10% fraction labeled (f=10%). The inset figure illustrates how base calling is made on a 10-base long homopolymer. The intersection between adjacent distributions is used as a cutoff. The area shaded in blue (left), red (right), and green (middle) represents the probability of a single deletion error, a single insertion error and a correct call, respectively.

FIG. 2E: The theoretical quality of bases called as a function of template numbers is calculated from the binomial distribution for various combinations of fraction labeled (f=5, 10 and 20%) and homopolymer length (L=5, 10, 20). The red line at 1% error highlights the template number required for calling Q20 bases (Q20=length of sequence that can be obtained with 1% error rate). These values are listed in Table 1.

FIGS. 7A and B: Monte Carlo simulations were performed using a misincorporation rate of 0.2% ($p_m$=0.002) and two additional sources of read error: the coefficient of variation for single dye intensity (c.v.=50%) and initial SNR for fluorescence detection (A: $SNR_0$=20 for N=1,000 and f=10%; B: $SNR_0$=50 for N=5,000 and f=5%). In this case, no incomplete extension is considered ($p_i$=0). Only results obtained using the ideal base caller are shown. Four combinations are shown: 1) no noise and no signal variation (magenta, right), 2) dye variation alone (cyan, $2^{nd}$ from right), 3) noise alone (green, $2^{nd}$ from left), and 4) both noise and dye variation (blue, left).

FIGS. 7C and D: Monte Carlo simulations were performed using either 1,000 (C) or 10,000 (D) templates and 10% fraction labeled. All potential sources of sequencing error were considered in the simulations. These include either a combined 0.1% misincorporation and 0.1% incomplete extension (blue and green), or a combined 0.2% misincorporation and 0.2% incomplete extension (cyan and magenta), with 50% coefficient of variation in dye intensity and SNR of 20 for the detection of 100 molecules (C: $SNR_0$=20 for N=1,000 and f=10%; D: $SNR_0$=200 for N=10,000 and f=10%). Read error rates from both the simple base caller (blue and cyan) and the ideal base caller (green and magenta) are shown. Q20 bases are indicated by the red line.

DETAILED DESCRIPTION OF THE INVENTION

A. Introduction

Figure 1:
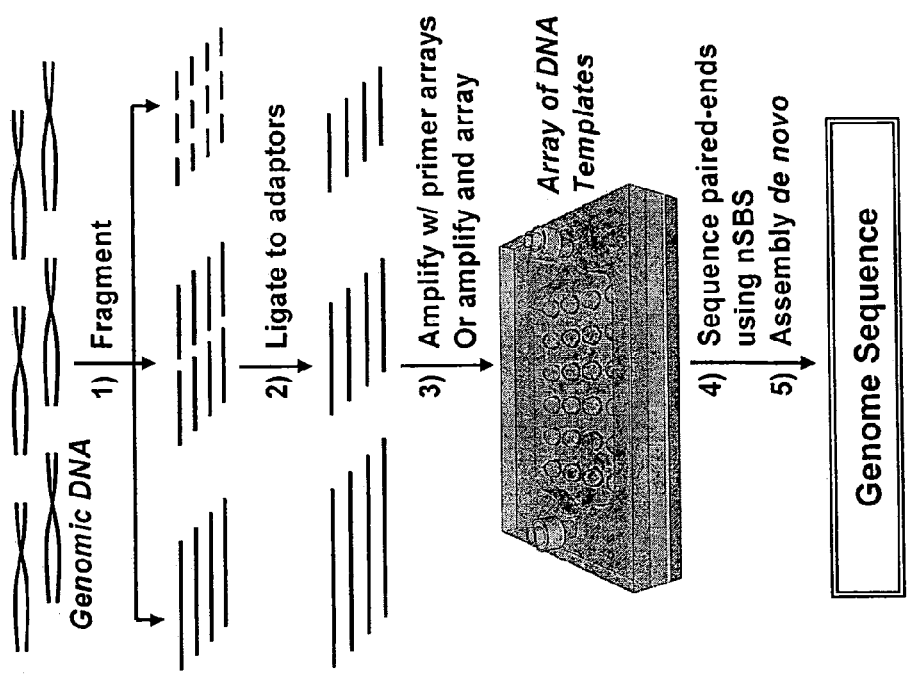
FIG. 1 shows a broad overview of a genome sequencing embodiment of the invention.

Disclosed is a new method for high throughput DNA sequencing called natural DNA sequencing by synthesis (nSBS). One aspect of the method is cyclic nucleotide-by-nucleotide DNA sequencing by synthesis involving the incorporation of a small percentage of non-terminating, fluorescently-labeled nucleotides (e.g., less than 20%, e.g., about 10%, 5%, or 1%, or 1-10%, 1-15%, 5-25%, 10-30%, 5-15%, 1-12%, 8-12%, 5-10%, or 5-12% of the total number of nucleotides incorporated in a given cycle) along with natural (unlabeled) nucleotides. The small percentage of labeled nucleotides minimizes the modification of the natural structure of the extending DNA template and the perturbation of the DNA polymerase, ensuring that subsequent DNA synthesis is minimally affected in the process. Optionally, the fluorescent labels can be cleaved off after the imaging step. Since DNA polymerases have intrinsically high fidelity and can synthesize long diverse DNA sequences, including homopolymer stretches, rapid sequencing with long reads and high accuracy can be achieved.

Compared to a pyrosequencing platform, the methods of the present invention can be scaled to much higher throughput with higher detection sensitivity, allowing for simpler sample preparation and lower reagent costs. Because fewer copies of DNA template are required (e.g., 10,000 compared to 1 million), more features (e.g., distinct area, spots, wells) can be packed onto a single chip. Unlike the 454 pyrosequencing method where multiple enzymes and real-time signal detection are required to monitor the SBS process, nSBS allows the DNA synthesis and signal detection steps to be decoupled. This provides at least the following advantages:

Better control of the extension time over the SBS process to achieve longer read lengths and higher accuracy;

Washing to remove residual nucleotides is more efficient using a planar surface (e.g., on a microfluidics platform) instead of a well structure. Thus, while a well structure can be used for the present nSBS methods, the flexibility of the current methods is advantageous. Washing can reduce read error due to carry-forward extension, which has turned out to be a major factor contributing to template de-synchronization in pyrosequencing;

With modern imaging devices such as an EMCCD camera with single molecule detection sensitivity, very few fluorescent dyes are required for high-speed quantitative imaging. As few as 10,000 copies of a template may be sufficient for achieving >500 base reads;

The reduced number of template copies allows the present system to be scaled to very high-density arrays for whole genome sequencing; and Fewer enzymes (only a DNA polymerase) and less reagent are required, resulting in a significant reduction in reagent costs. Because few labeled nucleotides are incorporated, and the labels can be removed after each incorporation step, a natural DNA polymerase can be used. Non-natural DNA polymerases can also be used, but often are more expensive.

Compared to technologies utilizing sequencing by synthesis with reversible terminating nucleotides (Terminator SBS), the present invention eliminates the need for highly engineered DNA polymerases by using mostly natural (unlabeled) nucleotides. Whereas read lengths are limited in Terminator SBS due to excessive desynchronization, the present methods can sequence long homopolymers with high accuracy.

In current SBS methods (e.g., Solexa/Illumina and Helicos), 100% of the nucleotides used are fluorescently labeled reversible terminators. This supposedly alleviates the difficulty in reading long homopolymer runs. The use of highly modified nucleotides, however, requires highly engineered DNA polymerases capable of incorporating these nucleotides. Incorporation of these nucleotides is often slow and inefficient. A residual moiety is left on every base after the cleavage of the fluorescent dye. This compounds the problem of incorporation efficiency. Improved template synchronization has been reported for methods using an additional reaction cycle with nucleotides with a protected 3'-hydroxyl group, but without the bulkier fluorescent dye. While these methods seek to increase the extension of any lagging strands, inefficient incorporation and cleavage cause the templates to go out of synchronization, resulting in only very short read lengths.

B. Definitions

"Sequencing by synthesis" (SBS) refers to methods of determining the sequence of a nucleic acid as it is being synthesized by an appropriate polymerase. In addition to the presently disclosed methods, which involve synthesis using mostly natural nucleotides, SBS methods include pyrosequencing and the Solexa/Illumina method.

The term "target DNA" or "template DNA" refers to a stretch of DNA to be sequenced according to the present methods. The term encompasses both complementary strands of the target DNA molecule. One of skill will understand that the sequence of one strand of target DNA reveals the sequence of the other strand due to familiar Watson-Crick base pairing. The target DNA can be attached to primers or adaptors, e.g., to facilitate amplification, synthesis, or attachment to a solid support.

A "DNA polymerase" is an enzyme that synthesizes a new strand of DNA in a 5' to 3' direction from a primer hybridized to a template strand of DNA. DNA polymerases are well-known in the art and commercially available. The DNA polymerase "reads" the template in the 3'→5' direction, and adds individual nucleotides (bases) to the new or nascent strand in the 5'→3' direction. The polymerase requires a 3'OH group from a primer to begin extension of a new DNA strand. Individual nucleotides (dNTPs, or dATP, dCTP, dTTP, dGTP, or A, C, T, G) are added according to the general mechanism described in FIG. 2. The particular base (A, C, T, or G) depends on the sequence of the template DNA, so that the new base hybridizes to the nucleotide on the template strand through a Watson-Crick interaction. The DNA polymerase cycles between "open" and "closed" conformations. The DNA polymerase is in the open position with the primer-template DNA complex. Once an incoming nucleotide enters the active site, the polymerase cycles to the closed position.

"Nucleic acid" or "oligonucleotide" or "polynucleotide" or grammatical equivalents used herein means at least two nucleotides covalently linked together. The terms "nucleotide" and "base" generally refer to individual monomers (e.g., dNTPs or rNTPs comprising adenine, thymine, uracil, cytosine, or guanine). Oligonucleotides are typically from about 5, 6, 7, 8, 9, 10, 12, 15, 25, 30, 40, 50 or more nucleotides in length, optionally up to about 100 nucleotides in length. Nucleic acids and polynucleotides are polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "nucleotide base" refers to one of the five nucleobases, i.e., cysteine, thymine, adenine, guanine, and uracil, or an analog thereof.

The term "probe" or "primer", as used herein, is defined to be one or more nucleic acid fragments whose specific hybridization to a sample can be detected. A probe or primer can be of any length depending on the particular technique it will be used for. For example, primers for priming a DNA or RNA polymerase reaction (e.g., PCR) are generally between 10 and 40 nucleotides in length, while nucleic acid probes for, e.g., a Southern blot, can be several hundred nucleotides in length. Primers can be used for the present sequencing methods to initiate synthesis using a DNA polymerase. The probe or primer can be unlabeled or labeled as described below so that its binding to the target or template can be detected. The length and complexity of the nucleic acid fixed onto the target element is not critical to the invention. One of skill can adjust these factors to provide optimum hybridization conditions.

A probe or primer can also be immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854). One of skill will recognize that the precise sequence of the particular probes can be modified to a certain degree, but retain the ability to specifically bind to (i.e., hybridize specifically to) the same targets or samples as the probe from which they were derived.

A "hairpin primer" is a primer that comprises two complementary stretches of sequence that can hybridize to one another and form a double-stranded hairpin structure. The complementary portions are connected by a number of non-hybridized nucleotides, usually less than 10.

The term "hybridized template" refers to a single-stranded polynucleotide hybridized to a complementary sequence such as a primer or a nascent strand of DNA or RNA extending from a primer. The hybridized portion is double-stranded. The template strand forms the basis for base pair-specific synthesis using a DNA or RNA polymerase.

The term "ligated template" refers to a template strand that is attached (ligated) to another polynucleotide, e.g., a primer or adaptor sequence.

The term "single nucleotide solution" refers to a solution of monomeric nucleotides, all comprising the same nucleotide base. For example, a single nucleotide solution can comprise a solution of nucleotides selected from one of the following nucleotides: dCTP, dATP, dGTP, and dTTP (or in the case of RNA sequencing, rCTP, rATP, rGTP and rUTP). The sequential, repeated addition of all four single nucleotide solutions is referred to as "cyclic." The sequence of the four nucleotides can be in any order, and can be the same for each cycle, or can differ between cycles. In some cases, the single nucleotide solution can comprise labeled and unlabeled nucleotides.

A "label" or a "detectable moiety" is a composition detectable by spectroscopic, photochemical, biochemical, immunochemical, chemical, or other physical means. The term label, as used herein, generally refers to a fluorescent label. Labels can also include, e.g., an affinity agent such as biotin, chemically reactive groups, electron-dense reagents, enzymes (e.g., as commonly used in an ELISA), or digoxigenin. Any method known in the art for conjugating a label can be employed, e.g., using methods described in Hermanson, *Bioconjugate Techniques* 1996, Academic Press, Inc., San Diego. The label can be directly attached to a nucleic acid, or indirectly attached via a linker, e.g., a cleavable linker such as a disulfide linker.

The term "paired end sequencing" refers to a method of sequencing each end of a stretch of DNA. Paired end sequencing is useful for determining the length of the segment of DNA that falls between two sequences. This is particularly valuable information for aligning genomic DNA sequences. Paired end sequencing can also be used to confirm or extend sequence reads from a template that has already been sequenced. The concept and method are discussed in more detail herein (see FIG. 3).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA). One of skill in the art will appreciate that specific hybridization between nucleotides usually relies on Watson-Crick pair bonding between complementary nucleotide sequences.

A "flowcell" or "flow channel" refers to a recess in a structure which can contain a flow of fluid or gas. Flowcells are commonly used on sample platforms, so that reagents can be added and removed from a given sample without moving the platform.

A "microfluidic device" refers to a device having one or more fluid passages, chambers or conduits which have at least one internal cross-sectional dimension, e.g., depth, width, length, diameter, etc., that is less than 1500 μm, and sometimes less than about 1000 μm, or about 500 μm, and typically between about 0.1 μm and about 500 μm.

A "control" sample or value refers to a sample that serves as a reference, usually a known reference, for comparison to a test sample. For example, a test sample can be an unknown sequence, and a control a known sequence.

One of skill in the art will understand which controls are valuable in a given situation and be able to analyze data based on comparisons to control values. Controls can be valuable for determining the significance of data. For example, if values for a given parameter are widely variant in controls, variation in test samples will not be considered as significant.

C. Overview of nSBS

The basic nSBS procedure entails performing cycles of stepwise DNA synthesis extension followed by a fluorescence detection and optional cleavage step.

In a sense, nSBS chemistry is similar to that of Sanger dideoxy-sequencing with 4-color fluorescently-labeled nucleotides because single nucleotides are added in an iterative fashion. But instead of the terminator dideoxyribonucleotides, fluorescently-labeled non-terminating dNTPs are used.

FIGS. 1 and 2B illustrate an exemplary workflow of nSBS, as follows:

1) Primers are hybridized to templates arranged on a high-density ordered array. The array can be produced, e.g., by in situ clonal amplification or assembled from pre-amplified DNA clones on microbeads. In some embodiments, the primers are hybridized to adaptor oligonucleotides of known sequence that are ligated to the desired template before the hybridization step. DNA polymerases can be pre-incubated with, and allowed to bind to, the primed templates at this stage, or added in step 2.

2) A single nucleotide solution (i.e., one containing a single type of dNTP, with a small percentage of the nucleotides linked to a cleavable fluorescent label) is introduced into the flow chamber and incubated for a very short period of time. A wash solution is flowed through the chamber to remove the unincorporated nucleotides (using, e.g., a flowcell and microfluidic system).

3) Quantitative fluorescence imaging of the whole substrate is performed by raster scanning (e.g., conversion of vector data to image data using a standard rasterization algorithm) with a high-speed imaging system.

4) If the particular nucleotide was incorporated (as determined in step 3), the fluorescent labels are cleaved off chemically or photochemically. Again, the chamber can be flushed with a wash solution. In some embodiments, the chemical or photochemical cleavage step occurs regardless of whether a signal is detected in step 3.

5) Steps 2-4 are repeated for the other three nucleotides. In some embodiments, steps 2-4 are practiced regardless of whether a signal is detected in step 3 (i.e., regardless of whether the first nucleotide was incorporated), so that the complete set of four nucleotide solutions is exposed to the template in each round. In some embodiments, the addition of the next single nucleotide solution depends on whether a signal is detected in step 3, so that the complete set of four single nucleotide solutions is not necessarily exposed to the template in every round. That is, if the first nucleotide solution results in a signal, the second, third, and fourth single nucleotide solutions are not added. If the second nucleotide solution results in a signal, then the third and fourth single nucleotide solutions are not added, etc.

6) Steps 2-5 can be repeated tens, hundreds, or thousands of times to sequence the desired template. The DNA polymerases can be replenished periodically to compensate for occasional dissociation from the primed DNA templates.

In some embodiments, a dNTP solution, comprising a mixture of all four unlabeled nucleotides can be added after synthesis/sequencing of any number of bases, so that the remaining portion of the nascent strand is synthesized by the DNA polymerase. Rapid completion of the nascent strand can be useful for paired end sequencing of larger templates (e.g., over 1000 or 10,000 bases) and for conserving more costly reagents.

Given the speed and fidelity of DNA polymerases, short reaction cycle times, on the order of 60-90 seconds, can be achieved. The sequencing speed is generally limited by the imaging system, which could take as long as a few minutes to scan through the whole substrate. Regardless, a few hundred cycles can be finished within a day. This is much faster than other SBS or SBL methods, which take a few days to over a week for a single sequencing run. A simple strategy for paired-end sequencing of genomic DNA libraries of various sizes can also be used for de novo sequencing and assembly of mammalian-size genomes.

D. Paired End Sequencing

The invention further provides methods of paired end sequencing. In brief, the technique is used to generate sequence information for both ends of a target sequence. The paired sequence information, combined with the distance between the sequences (if any), can be used in combination with known assembly programs for assembly of genome-sized sequences. Paired end sequence information, gathered in massive parallel for hundreds or thousands of genomic fragments (each representing an individual template or target DNA sequence) can be compiled for assembly of genomic sequence.

Figure 3:
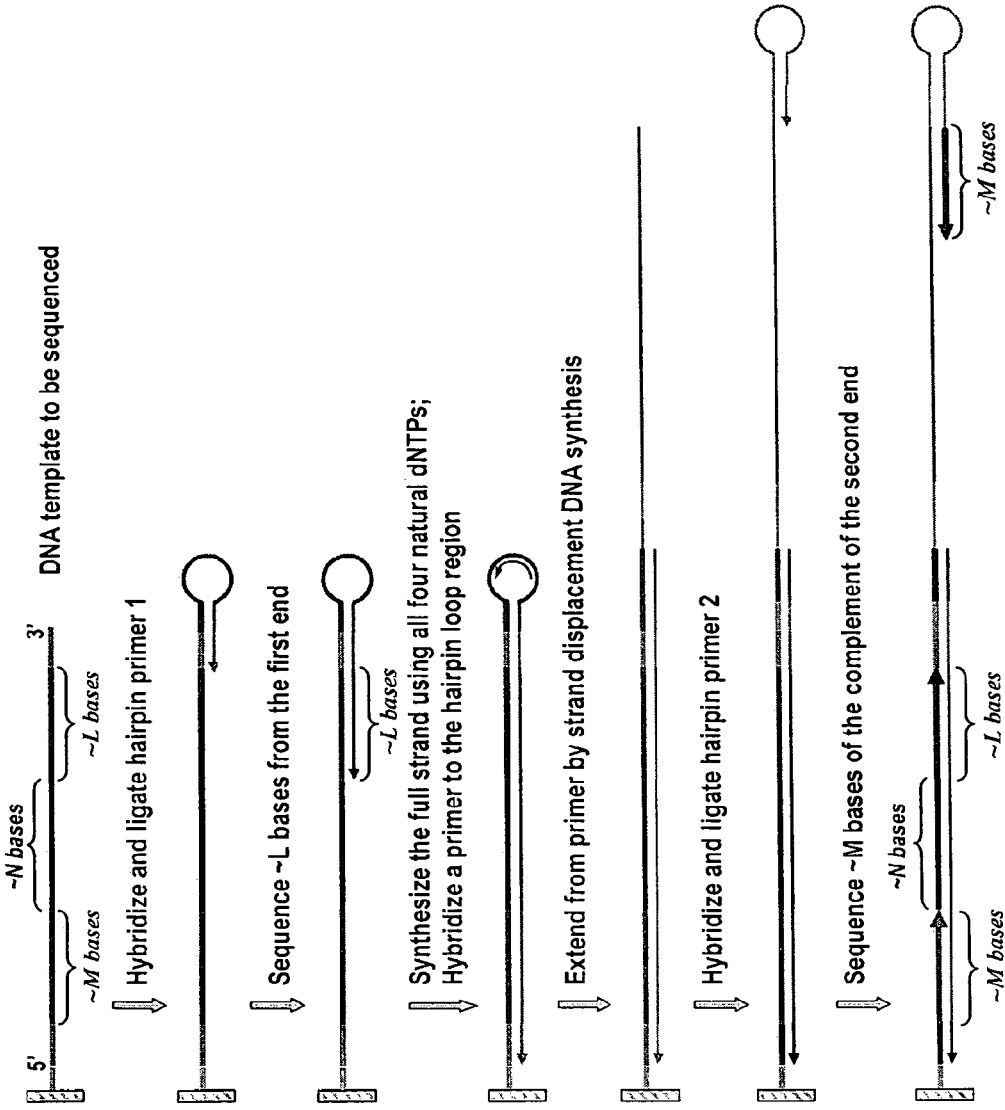
FIG. 3 shows the paired end sequencing strategy. Once the template DNA is amplified, hairpin primer 1 is attached (ligated) to the 3' end. Sequence is obtained from the 3' end of hairpin primer 1 using nSBS. In the displayed embodiment, a primer is hybridized to at least a portion of hairpin primer 1, and DNA is synthesized from that primer. Sequence information can optionally be obtained during this extension step, e.g., for confirmation or additional sequence. Hairpin primer 2 is then attached to the 3' end of the longer strand, and sequence is obtained from the 3' end of hairpin primer 2. The sequence obtained in this step is at the other end of the target DNA sequence. Using the paired end strategy, both ends (L and M segments) of a target DNA can be sequenced. In the displayed embodiment, L and M segments are separated by an N segment that is not sequenced.

The method is outlined in FIG. 3. A hairpin primer is attached to one end of a polynucleotide comprising the target sequence. In the first read, a sequence representing the 3' end of the target sequence is determined according to the methods disclosed herein, from the 3' end of the hairpin primer. In some embodiments, a relatively short read of sequence is determined, e.g., 50, 100, or 500 bases, or, e.g., 1, 5, 10, or 15% of the target DNA sequence. In some embodiments, the remaining target DNA sequence is synthesized without determining the sequence, e.g., using a mixture of all four dNTPs that are not labeled.

Once the polynucleotide comprising the target DNA is synthesized, the 3' end of the extended strand is complementary to the 5' end of the target DNA sequence. A second primer sequence is then hybridized, e.g., to the hairpin primer, an adaptor sequence attached to the target DNA, or some portion thereof. In some embodiments, before addition of the second primer, the extended DNA molecule (double-stranded) can be denatured, e.g., using high temperature or a denaturant such as formamide. Denaturation is not necessary in many cases, as DNA polymerases are capable of strand displacement, and can synthesize DNA from the primer regardless of whether the template is single- or double-stranded. In the second read, the target DNA is again synthesized in the same direction and over the same length as in the first read. In some embodiments, sequence information is obtained during the second read, e.g., for confirmation or to obtain a longer read. In some embodiments, the target DNA is synthesized without resequencing (e.g., using a mixture of unlabeled dNTPs with the DNA polymerase). In some embodiments, the second read is omitted, so that the method proceeds directly to the next step (the third read).

In the third read, a hairpin primer is attached to the 3' end of the extended strand, and again, DNA synthesis is initiated. Sequence information is generally obtained in the third read. The sequence obtained in the third read represents the 5' end of the original target DNA. Accordingly, both ends of the target DNA sequence are obtained. Again, in the third read, any amount of sequence information can be obtained during this read. Again, the remaining DNA strand (if any) can be synthesized without determining the sequence.

In some embodiments, paired end sequencing yields the sequence of the entire target DNA. In some embodiments, paired end sequencing results in only a small portion of the total target DNA being sequenced. In some embodiments, the size of the target DNA is determined prior to the initiation of sequencing. In some embodiments, the size is determined after paired end sequencing.

Paired end sequencing is useful for a number of applications. In addition to assembly of large genomic sequences de novo, these include (i) single nucleotide polymorphism (SNP) detection, based on the consensus of an alignment of reads to a reference genome and (ii) large structural polymorphism detection using End Sequence Profiling (ESP) (Volik et al., Genome Res 16, 394-404 (2006)). Pair-wise alignment across these small structural polymorphisms can be problematic with short reads. Furthermore, they are small enough in scale to be indistinguishable from clone length variation and remain hidden from detection using ESP. These problems can be overcome using actual resequencing data gathered according to the present methods.

The paired end sequencing methods can be used to resequence by constructing a comparative-grade de novo assembly (comparative assembly). Entire contigs can be aligned against a reference genome as an alternative to the standard of aligning individual reads. The use of a comparative assembly targets the detection of both SNPs and fine-scale structural variation of a genome. Comparative assemblies of short reads sequenced from each end of, e.g., a 0.5 to 1 Kb template, can be used instead of a stratified library of cosmid and BAC clones. The small template size can advantageously be sequenced in parallel without library construction, which can resolve repeat polymorphisms that confound alignment- and ESP-based methods.

E. Reagents and Methods

The invention provides routine molecular biology techniques, e.g., for DNA manipulation and cloning. Polynucleotide sequences of the present invention include those that encode DNA and RNA polymerases, template polynucleotide sequences (e.g., genomic fragments to be sequenced), primers, and adaptor molecules, as described herein. Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994); Kriegler, Gene Transfer and Expression: A Laboratory Manual (1990); and Current Protocols in Molecular Biology (Ausubel et al., eds., 1994-1999). Nucleic acids can be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds).

1. Nucleic Acid Polymerases

DNA (and RNA) polymerases are enzymes that direct the synthesis of DNA (and RNA) in a template specific manner from individual nucleotides. The structures and enzymatic mechanisms are among the best characterized of almost all proteins, and frequently used as textbook examples for enzyme catalysis and specificity.

For simplicity, we refer to DNA synthesis, and sequencing using a DNA polymerase. However, the methods of the invention can be extended to detect sequences using an RNA polymerase or reverse transcriptase.

A variety of polymerases can be used, many of which are commercially-available. At least five families of DNA-dependent DNA polymerases are known, although most fall into families A, B and C. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I, II, and III (analogous to family A, B, and C, respectively). In eukaryotic cells, three different family B polymerases, DNA polymerases α, δ, and ∈ are implicated in nuclear replication, and a family A polymerase, polymerase γ, is used for mitochondrial DNA replication. Other types of DNA polymerases include phage polymerases. Any of these polymerases, combinations of all or portions of these polymerases, as well as chimeras or hybrids between two or more of such polymerases or their equivalents can be used to form a portion or all of the polymerase domain of hybrid polymerases of the invention.

Examples of DNA polymerases that can be used include without limitation: phi-29, Taq, T7, *E. coli* Klenow (from DNA pol I), *E. coli* DNA pol III, and *Baccilus stearothermophilus* (Bst) DNA pol. The DNA polymerase can also be genetically engineered, e.g., a hybrid (e.g., Phusion DNA polymerase in which a domain with strong dsDNA binding affinity is fused to a DNA polymerase to enhance processivity). Many useful DNA polymerases are commercially available (e.g., T7 DNA pol, Sequenase version 2.0™). Highly processive polymerases include phi29 and T7 DNA polymerases, and Moloney murine leukemia virus (M-MLV) reverse transcriptase. One of skill in the art will appreciate that DNA polymerases are structurally similar, and that recombinant, hybrid polymerases can be engineered using homologous domains from different polymerases.

In some embodiments, to avoid the potential for differences in the incorporation efficiency of labeled nucleotides, a DNA polymerase and labels that maximize incorporation efficiency and minimize incorporation variability are used. Several DNA polymerases can efficiently incorporate the fluorescently-labeled dNTPs along DNA templates to produce very uniform fragments independent of the sequence context, and these polymerases are used in most automated Sanger/dideoxy-based methods using capillary-array DNA sequencers. A number of natural and engineered DNA polymerases are capable of incorporating fluorescently-labeled deoxyribonucleotides (Reeve & Fuller *Nature* 376, 796-97 (1995); Rosenblum et al., *Nucleic Acids Res* 25, 4500-04 (1997); Ramanathan et al. *Anal Biochem* 337, 1-11 (2005); Aksyonov et al., *Anal Biochem* 348, 127-138 (2006); Tabor & Richardson, *J Biol Chem* 265, 8322-28 (1990); Zhu et al., *Nucleic Acids Res* 22, 3418-22 (1994); Zhu & Waggoner *Cytometry* 28, 206-211 (1997); Randolph & Waggoner *Nucleic Acids Res* 25, 2923-29 (1997); Mitra et al., *Anal Biochem* 320, 55-65 (2003); Anderson et al. *Biotechniques* 38, 257-264 (2005)).

2. Labeled Nucleotides

In some embodiments, the labeled nucleotides to be used in the present methods are optimized to incorporate long flexible linkers. These linkers present less hindrance to the DNA polymerases. The linker is attached to the nucleotide on the nucleotide base, or some other site that does not interfere with polymerization. Consideration of these factors results in higher step-wise incorporation efficiencies, fewer templates falling out of synchronization, and longer read lengths.

A variety of labels/dyes can be used, and are known in the art. The most common ones are fluorescein, cyanine dyes (Cy3 to Cy7), rhodamine dyes (e.g. rhodamine 6G), the Alexa series of dyes (Alexa 405 to Alexa 730). The Alexa series of dyes from Invitrogen cover the whole spectral range, and are very bright and more photostable than other dyes. In some embodiments the dyes are:

1. photostable (e.g., to prevent photobleaching);
2. bright (with high extinction coefficients for absorption and high quantum yields for emission);
3. small (to minimize structural perturbation);
4. not self-quenching; and
5. excitable using available light sources and detectable using commercially available cameras such as EMCCD or CMOS cameras.

Figure 5:
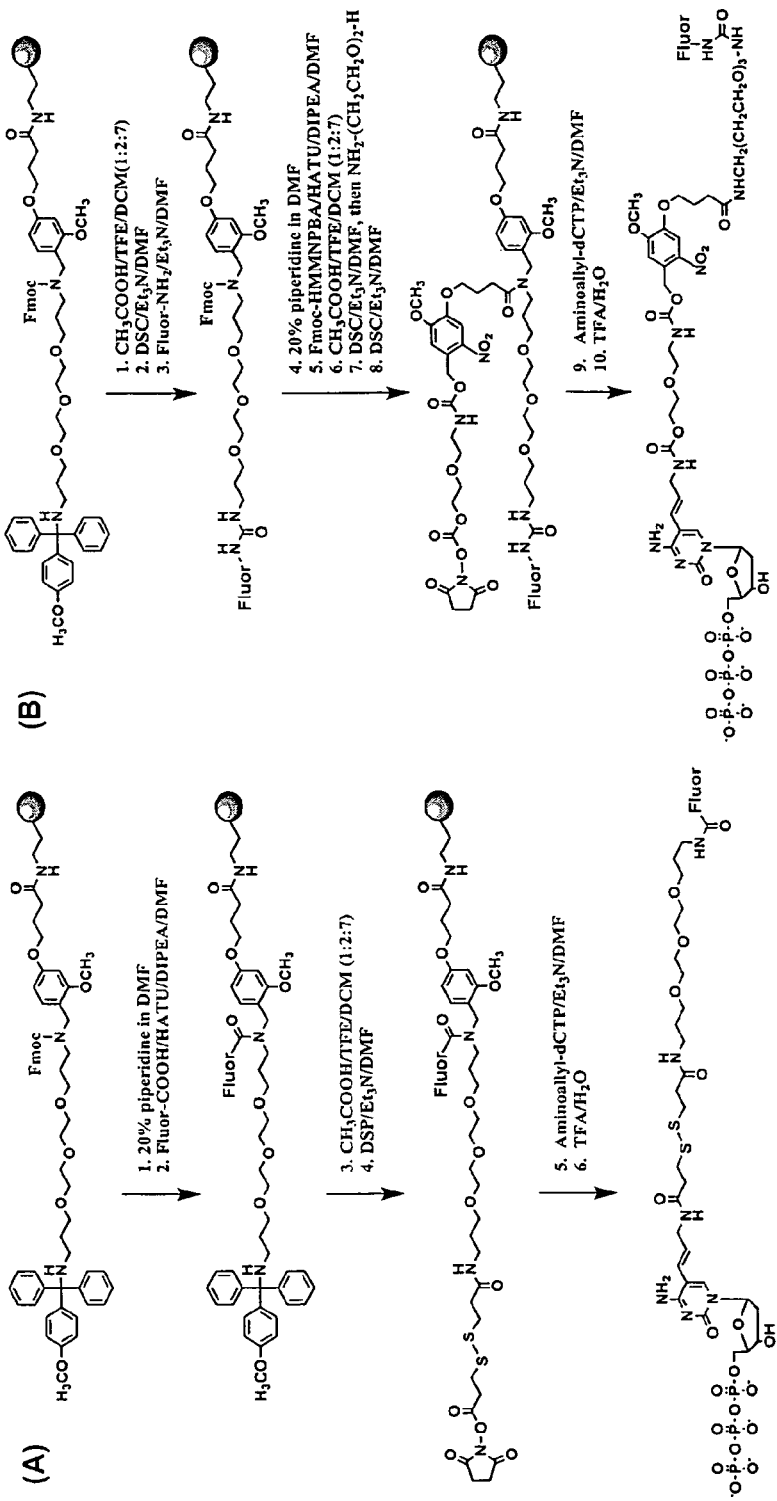
FIG. 5 shows examples of solid phase synthesis of fluorescently-labeled deoxyribonucleotide triphosphates with (A) chemically and (B) photochemically cleavable linkers. Only dTTP is shown, however, one of skill will recognize that other nucleotides can be synthesized in the same manner. Fmoc: 9-fluorenylmethyl carbamate; HATU: N,N,N',N'-Tetramethyl-O-(7-azabenzotriazol-1-yl)uronium hexafluorophosphate; TFE: tetrafluoroethylene; DCM: dimethylchloromethane; DMF: N,N-dimethylformamide DIPEA: N,N'-Diisopropylethylamine; DSP: Dithiobis-succinimidylpropionate; Et3N: Triethylamine; DSC: disuccinimidyl carbonate. The solid spheres indicate polymeric solid supports/beads.

Labeled nucleotides can be purchased (e.g., Cy5-S—S-dNTPs from Perkin Elmer), or synthesized according to standard methods. For example, FIG. 5 shows methods for solid phase synthesis of fluorescently-labeled dNTPs with either chemically or photochemically cleavable linkers to be used in nSBS. The advantage of photochemical cleavage is that it is faster, but both chemical and photochemical cleavage can be quickly and efficiently accomplished using the flowcells and microfluidics on the surface of the array.

Starting with commercially available amine-labeled dNTP's (e.g., aminoallyl-dNTP and propargylamino-dNTPs from Trilinks Biotechnologies, Jena Biosciences and PerkinElmer) and NHS-labeled fluorescent dyes (e.g., Invitrogen, GE Health Sciences etc.) the synthesis of fluorescently labeled dNTP's is quite straightforward Amine-labeled dNTP and NHS-labeled Alexa fluor and Cy3 and Cy5 dyes are available commercially for the synthesis. Solid phase synthesis of new labeled nucleotides with long linkers can be used and optimized for facile and efficient incorporation of modified nucleotides by DNA polymerases.

The synthesis involves only a few reaction steps on a solid support. The synthesis can be performed manually or automated (e.g., with an ABI 394 DNA synthesizer). Pre-activated solid supports are available commercially (e.g. Universal PEG NovaTag resin from NovaBiochem). All other reagents are also available commercially. The same solid support can be used for the synthesis of labeled nucleotides with, for example, either chemically cleavable disulfide linker or photochemically cleavable 2-nitrobenzyl linker.

The nature and length of the linkers affect the incorporation efficiency of labeled nucleotides by different DNA polymerases. With the versatile solid phase synthesis method, nucleotides can be synthesized with a variety of fluorescent dyes (e.g., Alexa and Cyanine series) and linkers of various lengths. PEG, pre-activated with a functional group, can be used. All of the reactions are standard reactions. While the final products are expected to be very pure, the products can be further purified by HPLC.

The labeled nucleotides can be combined with unlabeled nucleotides to form a single nucleotide solution for each type of nucleotide (e.g., dATP, dCTP, dGTP, dTTP). Each nucleotide can be labeled with the same label, or with different labels. The percentage of labeled nucleotides in each single nucleotide solution is generally the same, but can be varied depending on incorporation efficiency for each type of labeled nucleotide (e.g., if differently labeled).

In some embodiments, the percentage of labeled nucleic acids in the single nucleotide solution is added so that a small percentage of labeled nucleotides is incorporated in each cycle (e.g., less than 20%, or about 15, 12, 10, 8, 7, 6, 5, 2, or 1%, or 1-10%, 1-15%, 5-25%, 10-30%, 5-15%, 1-12%, 8-12%, 5-10%, or 5-12% of labeled nucleotides incorporated). In some embodiments, the percentage of labeled nucleotides in the single nucleotide solution is higher than the percentage that is incorporated into the nascent strand by the DNA polymerase, so that the percentage of labeled nucleotides in the single nucleotide solution is greater than 10 or 20%. In some embodiments, the percentage of labeled nucleotides in the single nucleotide solution is about 20, 30, 40, 50, 60, 70, 80, or 90% of total nucleotides in the solution.

The efficiency of incorporation of labeled nucleotides (as opposed to non-labeled nucleotides) will differ, depending on, e.g., specific reaction conditions, the type of label and linker, and the DNA polymerase used in the reaction. Once these variables are determined, one of skill can readily determine the percentage of labeled nucleotides that must be present in the single nucleotide solution to result in the desired incorporation rate. For example, side-by-side test reactions, with varying amounts of labeled nucleotides in the single nucleotide solution, can be run to determine the percentage necessary to achieve the desired small incorporation rate (e.g., about 1-10%).

3. Preparation of Genomic DNA

Genomic DNA can be randomly fragmented into various sizes (0.5 kb to 10 kb) using hydrodynamic mechanical shearing with relatively narrow size distributions (Thorstenson et al., *Genome Res* 8, 848-855 (1998); Roe, *Methods Mol Biol* 255, 171-187 (2004)). Methods of fragmenting and/or shearing genomic DNA are known in the art, including, e.g., sonication, nebulization, and enzymatic methods. Specialized devices for size-restricted DNA shearing are commercially available (e.g., Bioruptor® from Diagenode)

In addition, our laboratory has designed an automated instrument with a 9-port motorized rotary valve for this purpose (Joneja and Huang (2009) *Biotechniques* 7:553-56). Genomic DNA libraries can be prepared as follows:

(1) The sheared DNA fragments are ligated to two different adaptors, one labeled with a digoxiginin (DIG) and the other labeled with a biotin and a bipartite oligo with reverse sequences linked by a 5'-5' linkage. A large excess of 5'-5' linkages (e.g. >100:1) will be used to prevent chimera formations. The linkers are designed not be ligated to each other.

(2) After ligation the DNA molecules containing a biotin moiety are captured onto streptavidin-coated superparamagnetic microbeads. Strand-displacement DNA synthesis is used to release one strand of the duplex DNA molecules.

(3) The released genomic DNA fragments containing a DIG are captured onto microbeads coated with anti-DIG antibodies.

(4) Another biotinylated adaptor is ligated to the captured templates. Each biotinylated DNA molecule is captured onto a streptavidin-coated nanoparticle or microbead. A large excess of particles or beads (e.g. nanoparticle: DNA=20:1) are used to ensure each DNA molecule will be attached to only one particle. Since most of the steps are performed on microbeads, recovery yield for each step is very high. Fluorescently-labeled and streptavidin-coated nanoparticles are available in sizes from 20 nm to several micrometers from many sources (e.g. Invitrogen).

(5) The DNA-nanoparticle conjugates are released from the anti-DIG beads.

4. Amplification of Template DNA

Template or target DNA sequences can be amplified according to any amplification method. An amplification reaction refers to any chemical, including enzymatic, reaction that results in increased copies of a template nucleic acid sequence Amplification methods are well-known in the art, e.g., polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)).

A number of variations on PCR have been developed. In particular, bridge PCR is useful for streamlined direct in situ amplification of a single DNA molecule (e.g., a genomic fragment, diluted to one copy per feature (e.g., well, chamber, or spot)) (Mikkelsen et al., *Nature* 448, 553-560 (2007); Barski et al., *Cell* 129, 823-837 (2007); Bentley *Curr Opin Genet Dev* 16, 545-552 (2006); Johnson et al., *Science* 316, 1497-1502 (2007); Robertson et al., *Nat Methods* 4, 651-657 (2007). Standard bridge PCR involves a uniform layer of 5' and 3' primers tethered to a planar glass surface. Adaptor primers are ligated to the target DNA according to standard methods. Bridge PCR has enabled low-cost sequencing on the Solexa/Illumina 1G Genome Analyzer, but the single molecules on that analyzer are randomly distributed onto the surface, and the resultant clonal clusters are not ordered. Furthermore, the sizes of clonal clusters are small (only ~1000 copies) and not uniform. This presents complexity in image processing and sometimes ambiguity in object alignments which result in lower throughput and shorter reads.

While the protocol can be varied, bridge PCR commonly comprises the following steps:

1) Ligate adaptor sequences to the target DNA sequence.
2) Attach two primers (primer 1 and primer 2) that are complementary to the adaptor sequences to a solid support.
3) Amplify the target sequence. During the first round of amplification, a first strand of target DNA, attached to the solid support, will be amplified from, e.g, primer 1. The 3' portion of the strand will be complementary to primer 2 on the solid support. The new strand will thus form a bridge on the solid support. Amplification then occurs from primer 2.
4) Continue to amplify to occupy as many attached primer sites as possible.

Figure 4:
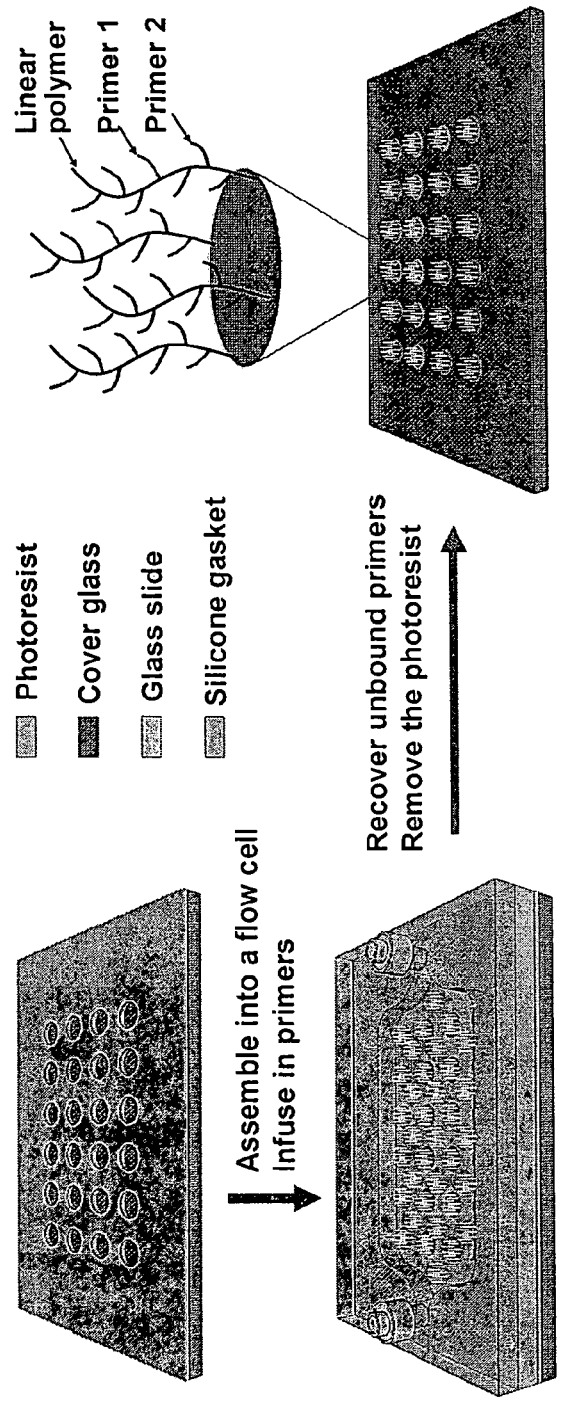
FIG. 4 shows fabrication of primer arrays for in situ DNA amplification. Shown here is the schematic of an array of primers tethered to linear polymers. These primers can be used for bridge PCR, hyperbranched rolling circle amplification (Lizardi et al. (1998) *Nature Genetics* 19:225-32) or other methods to amplify a template DNA before sequencing. Amplifying template DNA on the linear polymers, so that several copies of the same sequence are attached to each polymer, allows for a very high concentration of template DNA in each distinct area or "spot" on the array. This in turn amplifies the signal obtained from the present nSBS sequencing methods. Arrays of primers in a monolayer structure on the array can be fabricated as well.

Standard bridge PCR is not very efficient, i.e., only a thousand copies of a template can be obtained with 40 PCR cycles (Fedurco et al., *Nucleic Acids Res* 34, e22 (2006)). Single molecule amplification by PCR with primers tethered to a thin layer of polyacrylamide has been shown to be very efficient (Mitra et al., *Anal Biochem* 320, 55-65 (2003); Mitra & Church *Nucleic Acids Res* 27, e34 (1999)). Thus, for the present methods, oligonucleotide primers are tethered onto linear polymers as carriers. Amplification on linear polymers more closely mimics reactions in solution. FIG. 4 illustrates primers attached to a linear polymer that can be used to amplify the target DNA in this way. The linear polymer can be a polynucleotide, polyacrylamide, or other soluble material that can facilitate attachment to an nucleic acid.

The methods disclosed herein offer improved efficiency over standard bridge PCR. Amplification is performed with a perfectly-ordered array of primers, either in a monolayer, or on a 3D structure with linear polymers, on a planar surface. The array serves 3 purposes: 1) ordering the amplified clones; 2) confining each clone within one feature of the array. The primers are physically limited within each feature by photoresist; 3) obtaining a uniform number of copies of each template DNA, with the assumption that nearly every primer will result in a single copy of the template.

As explained above, the template copy number can be further increased (to increase signal intensity) using a flexible, linear polymer. Primers tethered to a linear copolymer of polyacrylamide labeled with biotin can be immobilized using the same biotin-avidin affinity capture mechanism. Arrays of primers with dual biotin-label and arrays of primers immobilized on microbeads via dual biotin label can survive many cycles of PCR or synthesis. It may be more desirable to have a covalent linkage between the primers or the linear polymers and the glass substrates. "Click chemistry" is used for facile covalent immobilization (Seo et al., *J Org Chem* 68, 609-612 (2003); Seo et al., *Proc Natl Acad Sci USA* 101, 5488-5493 (2004); Wu et al., *Angew Chem Int Ed Engl* 43, 3928-3932 (2004); Rozkiewicz et al., *Chembiochem*, DOI: 10.1002/cbic.200700402 (2007)). This can be carried out easily by derivatizing the glass surface with an azide group and primers/polymers with an alkyne group (or vise versa) using commercially available reagents. Mussel-inspired surface chemistry can also be used for multifunctional surface coatings. (Lee et al., *Science* 318, 426-430 (2007)).

Assuming a planar surface, a thermocycler with an Alpha Twin Tower block (MJ Research) is used for in situ PCR amplification of up to 32 slides simultaneously. The template DNA molecules can be hybridized to primers on an array, and the slide sealed with a Frame Seal chamber (MJ Research). The slide assembly is placed in the alpha block and PCR amplification is performed. A flow device with built-in thermoelectric modules for programmable rapid thermocycling and a microfluidic system for reagent delivery and washing can be used. The device has an observation window and can be mounted onto a microscope for real time imaging.

5. Array Fabrication

In some embodiments, the nucleic acid molecules are attached to a solid support for sequencing. For example, in some embodiments, the target DNA is amplified so that it is attached to a solid support (as described above), and ready for sequencing. The solid substrate can be arranged, e.g., in an array on a flat surface, in a spot array, or on beads. Common substrates for this purpose include glass and quartz slides. The array format is convenient because the present technology is designed to gather measurements from more than one DNA polymerase simultaneously.

Using the example of an array format, a wide variety of capture area sizes (spots for capturing the polymerase molecules) can be employed. The substrate can comprise wells and/or spot sizes of a predetermined size and density, e.g., spot sizes of approximately 50 nm or smaller. The pattern of wells or spots can provide particular information such as bar code information. The substrate can also contain materials used to generate a reference measurement or control signal for either the assay or the signal readout, or may be simply used as a locating device on the substrate.

Methods of attaching nucleic acids to a substrate are known in the art. Polynucleotide molecules can be fixed to the substrate using a variety of techniques, including covalent attachment and non-covalent attachment.

Biotin or avidin can be attached to the polymerase (e.g., on a side chain of a particular amino acid by conventional methods), and avidin or biotin fixed on the substrate to effect binding. Functional groups and reactions that can be used for immobilization include:

Sulfhydryl—bromoacetyl reaction
Sulfhydryl groups (under oxidizing, alkaline conditions)
Amino—aldehyde reaction
Sulfhydryl—aldehyde reaction
Hydroxyamino—aldehyde reaction One of skill will appreciate that these methods can be used with intermediate linker molecules as well. PEG is commonly used as a linker. The substrate can also be treated to improve binding of the linker or reactive group. Gold and polyelectrolyte multilayer are examples of treatments for solid substrates.

In some embodiments, the polynucleotides are immobilized on a substrate. In some embodiments, the template is primed with a complementary oligonucleotide before immobilization, while in some embodiments, the hybridization occurs after immobilization. In some embodiments, the primer oligonucleotide can perform a dual function, and be used as a capture probe to immobilize the template to the substrate. Such a dual function oligonucleotide will be attached to the substrate closer to the 5' end of the oligonucleotide, leaving the 3' end available for hybridization to the template, and the 3' hydroxyl group available for addition of nucleotide bases by a polymerase. Such a primer can include modified, nuclease-resistant bases, or can comprise PNA molecules.

In some embodiments, the substrate includes capture probes that hybridize with the polynucleotide molecule. An adaptor oligonucleotide, e.g., between the template and capture probe, can also be used. In some embodiments, the adaptor oligonucleotide is ligated to the template, and hybridizes to the capture probe. In some embodiments, the adaptor is a polynucleotide (e.g., polyA), which can be added with a terminal transferase, and will hybridize to a capture probe. In some embodiments, capture probes can comprise oligonucleotide clamps, or like structures, that form triplexes with adaptors, as described in Gryaznov et al., U.S. Pat. No. 5,473,060.

A surface can have reactive functionalities that react with complementary functionalities on the polynucleotides to form a covalent linkage (see, e.g., Smirnov et al. (2004), *Genes, Chromosomes & Cancer*, 40: 72-77; Beaucage (2001), *Current Medicinal Chemistry*, 8: 1213-1244. Long DNA molecules (several hundred bases) can also be efficiently attached to hydrophobic surfaces, such as a clean glass surface that has a lower concentration of reactive functionalities, e.g., —OH groups.

Polynucleotide molecules can be adsorbed to a surface through non-specific interactions with the surface, or through non-covalent interactions such as hydrogen bonding, van der Waals forces, etc. Attachment may also include wash steps of varying stringencies to remove incompletely attached molecules or other reagents.

An exemplary array fabrication method is illustrated in FIG. 4. Wafer-scale highly-ordered arrays of immobilized primers can also be routinely fabricated using digital methods. By using the photoresist to protect the areas between features (e.g., spots, wells), the primers are immobilized only on the bottom surface of the wells. After the removal of the photoresist, any non-specifically bound primers on the areas protected by the resist can be removed. The resulting array has virtually no background. Genomic DNA can be amplified by in situ parallel DNA amplification using the linear polymer array.

The invention can include methods for rapid assembly of high-density arrays of DNA templates to maximize imaging throughput and to simplify image processing (Barbee & Huang (2008) *Analytical Chemistry* 80, 2149-2154). A custom-designed flowcell and a high-speed fluorescence imaging system such as the one shown in FIG. 2A can be used. In nature, DNA synthesis by DNA polymerase is extremely rapid and accurate, so that each cycle time can be on the order of 90 seconds. The imaging system can be limiting, but an entire substrate containing a tens to hundreds of millions of genomic DNA fragment clones on a single substrate can potentially be sequenced in a matter of minutes. A few hundred cycles can be finished within several hours. This is much faster than the days or weeks required by other SBS or SBL methods that employ 100% labeled or reversible terminators. With a potential read length of up to 1,000 bases, nSBS can potentially be used for de novo sequencing and assembly of mammalian-size genomes.

F. Materials and Instrumentation

The processes and components for performing the sequencing reactions and fluorescence imaging are very amenable to automation. The components for positioning, reagent delivery and temperature control, and so on, can be incorporated into a microscope-based imaging system. In some embodiments, a programmable temperature controlled chamber with multiple flow cells is used for precise delivery of reagents into cells containing arrays of DNA templates. A prototype flow cell is shown in FIG. 4. The imaging chamber can be integrated into a microscope-based epifluorescence imaging system as shown in FIG. 2A. The flow cell is formed by the cover glass containing the arrays bonded onto a top glass plate which is patterned with flow channel(s) by photolithography and etching. The optical components for the ultra-fast 4-camera fluorescence imaging are based on a Zeiss Axio Observer microscope In some embodiments, DNA-conjugated microbeads are assembled into highly ordered arrays with virtually no background using a magnetic field gradient. Single DNA molecules can be amplified to a uniform number of templates on a glass surface patterned with highly ordered arrays of primers, or primers tethered to linear polymers. By matching the spacing of the highly ordered arrays to the imaging system, each template/feature can be imaged with only 9 pixels on a 1-Megapixel electron multiplying charge coupled device (EMCCD) camera. The process can be scaled even further to achieve an imaging efficiency of 4 pixels per feature. Both in situ amplification and post-amplification assembly can be used to generate high density arrays of DNA templates from genomic DNA fragments (more than 1 billion molecular clones in 4×4 $cm^2$).

In some embodiments, nSBS sequencing chemistry is optimized to reduce the cycle time (4 nucleotide flows) to 60 s. For such high-throughput methods, fluorescence imaging of the high-density arrays can be the bottleneck in the overall sequencing process. For example, to measure fluorescence from an array on a 1 cm×4 cm with a 20× objective and a 1-Megapixel EMCCD camera with 8 µm×8 µm pixel size, 2,500 images need to be acquired. With the singe molecule sensitivity of the EMCCD camera, an image with very good signal to noise can be obtained in 30 ms. Images can be acquired at the maximum camera read out speed of 35 MHz (35 frames/s). This is feasible with the frame-transfer camera since only single color imaging is required for nSBS and wavelength switching is not required. To image the array on 1 cm×4 cm will take about 70 s. Commercially available motorized microscope stages with linear encoders can be used for accurate position and fast scanning (Ludl Electronics Product).

A faster approach is to use a 4-camera system and ultra-fast piezo-ceramic stages (available from Physik Instrumente), which can move from field to field within 30 ms, for high data throughput. Four 1-Megapixel EMCCD cameras (iXon+ DV885, 35 Megapixels/s, Andor Technologies) will be used for imaging. A 4-way image splitting mirror can be used in the emission light path of a Zeiss Axio Observer with 4 camera ports (left, right, front and bottom). The flat and large field of view (25 mm) of the microscope is covered almost exactly by four cameras. The total maximum throughput of the system will be 140 Megapixels/s. To image a 1 cm×4 cm flow cell with a 20× objective will take only 40 s (~20 s for imaging+20 s stage movement) and the overall maximum data throughput will be ~70 Megapixels/s or 250 Gigapixels/hr. Using current imaging efficiency of 9 pixels/DNA template and an average of 2-3 bases per one complete cycle with 4 dNTP's, the sequencing throughput can be ~17 Giga bases/hr (17 billion bases per hour) or ~400 billion bases per day. Improving imaging efficiency to 4 pixels/template will allow a throughput approaching 1000 billion bases per day.

G Computer Systems

The calculations for the methods described herein can involve computer-based calculations and tools. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In some embodiments, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

H. Kits and Reaction Mixes

The present invention provides kits and reaction mixes for conducting nSBS. The components will depend on the particular aspect of nSBS for which it is designed (e.g., labeling nucleotides, assembling template arrays, sequencing or paired end sequencing). The kit will generally include instructions for conducting nSBS reactions using the components of the kits.

A reaction mixture for making labeled dNTPs can include single nucleotide mixes (e.g., a solution of each of the following nucleotides: dATP, dCTP, dGTP, dTTP), dyes, linkers, and appropriate reagents, as described herein.

In some embodiments, the single nucleotide solution already contains the appropriate percentage of labeled nucleotides, such that a small percentage of labeled nucleotides is incorporated in each cycle (e.g., less than 20%, about 15, 12, 10, 8, 7, 6, 5, 2, or 1%, or 1-10%, 1-15%, 5-25%, 10-30%, 5-15%, 1-12%, 8-12%, 5-10%, or 5-12% labeled nucleotides incorporated). In some embodiments, the percentage of labeled nucleotides in the single nucleotide solution is higher than the percentage that is incorporated into the nascent strand by the DNA polymerase, so that the percentage included with the kit solution is greater than 10 or 20%. In some embodiments, the percentage of labeled nucleotides in the single nucleotide solution is about 20, 30, 40, 50, 60, 70, 80, or 90%, or 10-50%, 20-60%, 50-80%, 10-20%, 20-30%, 30-40%, 40-50%, 50-60%, 60-70%, 70-80%, or 80-90% of total nucleotides in the solution. The percentage of labeled nucleotides in each single nucleotide solution is generally the same, but can be varied depending on incorporation efficiency for each type of labeled nucleotide (e.g., if differently labeled).

In some embodiments, the reaction mixture includes components for DNA synthesis. Such components can include any combination of the following: DNA polymerase; dNTPs; various single nucleotide solutions, each comprising a percentage of labeled nucleotides; adaptor sequences (e.g., to ligate to the end of the target DNA); primers; hairpin primers; and various buffers and salts. The kit can also include reagents for shearing DNA; reagents for cleaving the label; wash reagents; and/or a control sequence of DNA. In some embodiments, each component is packaged separately in the kit, e.g., so that each component can be added at an optimized dilution for the particular reaction conditions. In some embodiments, the kit includes are separate reaction mixtures for each single nucleotide, which can be added in a cyclic fashion as described above.

Kits designed to immobilize template DNA, e.g., on a surface or on a linear polymer, can include conjugation materials as described herein. In some embodiments, the kit includes the solid support to be used, which can vary based on the compatibility with the user's imaging system. In some embodiments, oligonucleotide primers are included, e.g., capture probe and/or oligonucleotides to be ligated to the template DNA sequences.

In some embodiments, the kit includes various reaction mixtures, e.g., as described above, while in some embodiments, the components are packaged or sold separately, but designed for use in combination. In some embodiments, the kit will include an appropriate substrate (e.g., treated glass slides), optionally including immobilized control sequences or primers to amplify target DNA (e.g., for bridge or rolling circle PCR).

Kits for sequencing/synthesis can comprise components for a reaction mix. A typical DNA polymerase reaction mix can include dNTPs; single nucleotide solutions; buffers (e.g., Tris); various salts (e.g., KCl, NaCl, $(NH_4)_2SO_4$, $MnCl_2$, Zn salts, $MgCl_2$); and often stabilizer, detergent, DMSO, and DTT. Kits of the invention can include additives to increase the specificity and efficiency of polymerase reactions.

It will be appreciated that kits of the invention also encompass any combination of the above-described components.

Instructions can be included with kits of the invention. A typical protocol for a kit, e.g., for sequencing using an immobilized template DNA, can include the following instructions:
Prepare template DNA (e.g., including isolation, amplification, removal of contaminants);
Ligate adaptor oligonucleotide sequence to the template DNA (e.g., to hybridize to a capture probe on the substrate, or to a primer sequence);
Immobilize DNA on a substrate;
Add primer oligonucleotide;
Add DNA polymerase and DNA polymerase reaction mix;
Add first single nucleotide solution;
Wash and detect signal, if present;
Add DNA polymerase and DNA polymerase reaction mix;
Add second single nucleotide solution, etc.

It will be appreciated that the above exemplary protocol can be varied using parameters well known in the art to optimize the conditions for efficiency and specificity of DNA polymerase activity. For example, synthesis of longer target nucleic acids may require longer incubation times and/or higher temperatures for efficient and specific amplification.

The invention also provides systems for practicing the present invention. For example, solid supports with distinct areas coated to attach to nucleic acids can be included, optionally with flowcell components. Such a system component can include e.g., glass slides, photoresist, cover glass, and other array components designed to be used according to the invention (see, e.g., FIG. 4). Additional system components can include the platform, e.g., as shown in FIG. 2A, microfluidic components, and optics as described herein. The system can also include a camera, e.g., an EMCCD camera. Additional components can include software that can be used to rapidly process imaging data. These components can be included in any combination, packaged separately, or as a single package.

The system will include components for practicing the invention, e.g., devices for supplying four different single nucleotide solutions to the nSBS reaction. For example, the system can have, as part of the microfluidics device, four containers for single nucleotide solutions with tubes or capillaries to supply the solutions to the nSBS reaction on the detection platform. The flow from the containers can be automated to run in a cyclic manner (i.e., all four in repeated succession) or based on detection of a signal. The system will also include devices for providing other reagents to the nSBS reaction, e.g., containers and supply routes for a mixed dNTP solution, wash solutions, DNA polymerase, cleavage reagents, etc.

It is understood that the examples and embodiments described herein are for illustrative purposes only and that various modifications or changes in light thereof will be suggested to persons skilled in the art and are to be included within the spirit and purview of this application and scope of the appended claims. All publications, websites, patents, and patent applications cited herein are hereby incorporated by reference in their entireties for all purposes.

I. Examples

Example 1 nSBS

Figure 2:
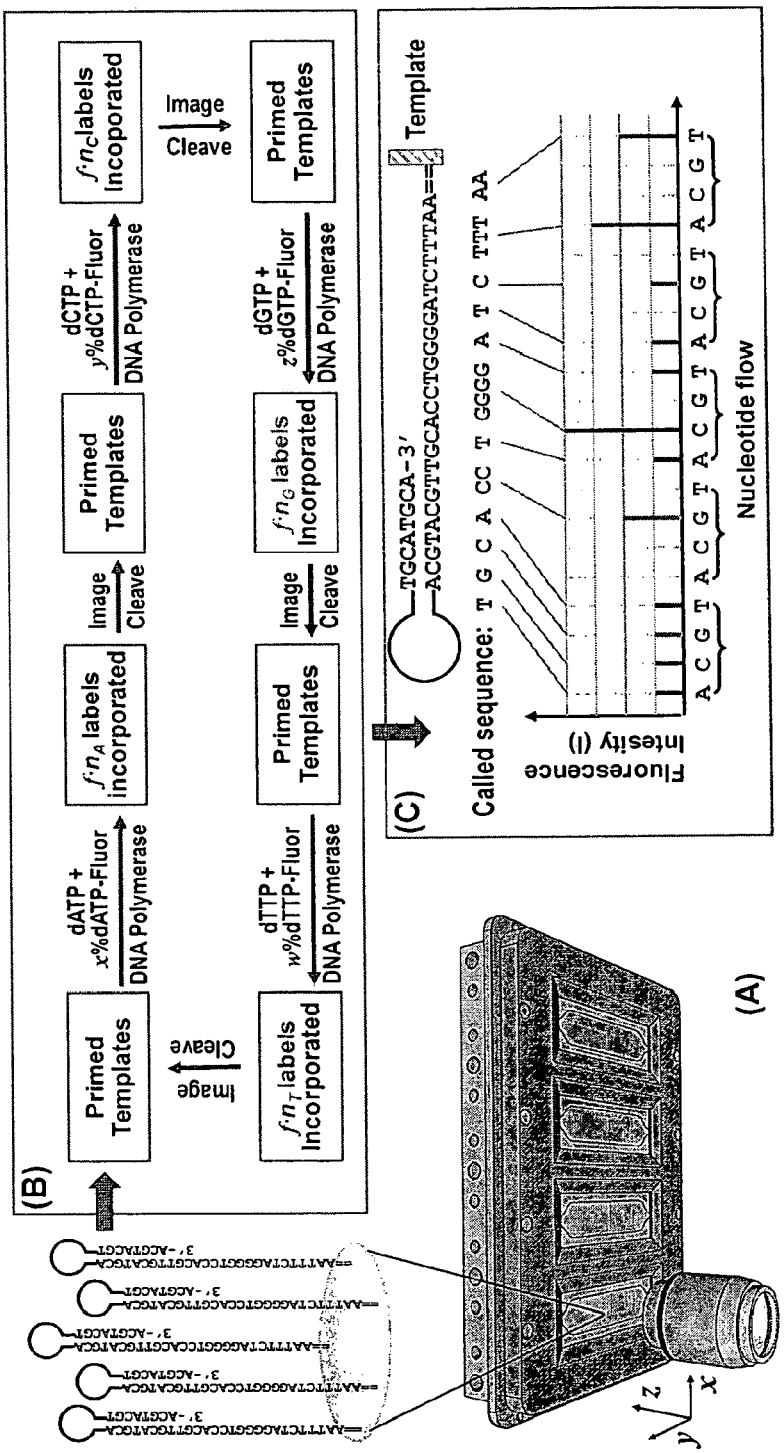
FIG. 2 shows the principle and theoretical error of nSBS.
Figure 2:
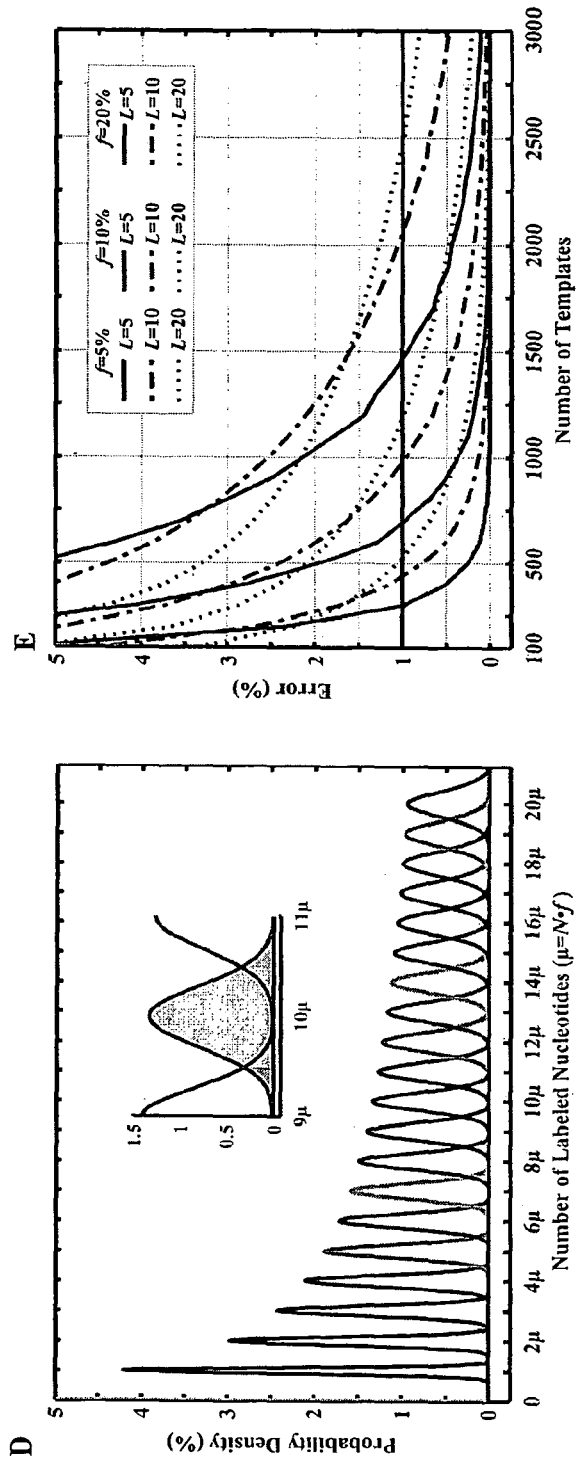

The example describes the feasibility of nSBS using a variety of PCR amplified DNA templates of known sequences with dual biotin labeled primers. The biotinylated templates will be immobilized and assembled into an array onto the surface of a cover glass coated with Neutravidin. The cover glass is then assembled into the flow cell (see, e.g., FIGS. 2 and 4). The basic principle and the workflow of nSBS are illustrated in FIGS. 1 and 2. Hairpin primers can be used to enable paired end sequencing (see FIG. 3) (Ju et al., *Proc Natl Acad Sci USA* 103, 19635-40 (2006)). The DNA polymerases can be bound onto the DNA template by pre-incubation of the polymerases with the primed templates and periodically replenished. A fully automated Zeiss 200M inverted fluorescence microscope system is used for quantitative measurement of the fluorescence from the templates after each addition of nucleotide. All the instruments are controlled by a computer and the whole data acquisition process is totally automated.

FIGS. 1 and 2 illustrate the basic principle of nSBS. The general procedure entails performing cycles of stepwise DNA synthesis extension followed by a fluorescence detection and cleavage step. Each cycle includes four nucleotide flows (one for each type of nucleotide) and each flow entails 3 steps:

(1) One of the four types of nucleoside triphosphates is flowed into the reaction chamber for a duration of 60-90 seconds. The nucleotide mix contains mostly natural nucleoside triphosphate but also some percentage of the same nucleotide labeled with a fluorescent dye molecule via a cleavable linker. The percentage of the labeled nucleotide in the nucleotide mix can be as high as 70% to achieve a desired labeled incorporation percentage of 10%. The total concentration of nucleotides in the mix could range from one to several micromolar. The nucleotides will be in a buffer appropriate for the specific DNA polymerase being used for sequencing. For example, if Bst DNA polymerase is used then the nucleotide mix might also contain 20 mM Tris, 50 mM KCl, 4 mM $MgSO_4$, 10 mM $(NH_4)_2SO_4$, and 0.1% Triton X-100 adjusted to pH 8.8. If desirable, the DNA polymerase and other necessary proteins can be preloaded onto the templates or added into the reaction mix, or both.

(2) After a brief washing to remove the reaction mix from the chamber (using a flowcell and microfluidic system), an imaging step is performed to measure the fluorescence intensity. The wash buffer contains 20 mM Tris, 50 mM KCl, 4 mM $MgSO_4$, 10 mM $(NH_4)_2SO_4$, and 0.1% Triton X-100 adjusted to pH 8.8. The imaging step involves illumination of the sample with an appropriate light source, e.g., a 473 nm diode laser for imaging fluorescein. TIRF microscopy on an Zeiss AxioObserver microscope is used to maximize light collection efficiency and reduce background noise. Using the appropriate filters for the dye being imaged, an EMCCD camera can collect the light emitted by the fluorescent dyes with an exposure time of 30 ms. A motorized stepper microscope stage can be used to perform rasterized scanning of the entire substrate. This can be necessary to acquire signal from every spot/feature on the array.

(3) The fluorescent labels are cleaved off either chemically or photochemically, followed by a more extensive washing using the same wash buffer to remove any residual nucleotides to prevent carry-forward extension in subsequent nucleotide flows. The sample is exposed to 350-370 nm light for a period of a few seconds to minutes in order to effect photochemical cleavage of the labels. Alternatively, palladium-catalyzed deallylation at 70° C. or disulfide reduction using 4 mM DTT can be used for chemical cleavage, depending on the chemistry used for the linker.

Example 2

Accuracy and Capacity of the nSBS Strategy

This example describes computer simulations of the accuracy of our sequencing strategy. These simulations utilize a theoretical model for base calling and Monte Carlo simulations to assess the feasibility of the method with random sequences from the human genome. Sequencing errors were calculated as a function of DNA template numbers, fraction of incorporated fluorescent labels and homopolymer read lengths. According to the calculations described herein, long homopolymer stretches up to 20 bases can be sequenced with high accuracy and Q20 (with 99% accuracy) using the methods of the invention. In addition, read lengths of up to 1,000 bases can be achieved with less than 10,000 copies of DNA template and 10% of the nucleotides in each incorporation step being labeled. The simulations also demonstrate that a Q20 read length of greater than 100 bases can be achieved, even if the sequencing is performed with 1,000 copies of template DNA and 10% labeled nucleotides incorporated.

All computations and simulations were performed with MATLAB (MathWorks). In the Monte Carlo simulations, the rand and randn functions were used to generate uniformly distributed and normally distributed pseudo-random numbers, respectively. The Mersenne Twister Algorithm was implemented in the pseudo-random number generators (Matsumoto & Nishimura (1998) *ACM Transactions on Modeling and Computer Simulation* 8: 3-30).

The analysis of nSBS shown here is based on some important assumptions. First, assume the probability of incorporating a fluorescently-labeled nucleotide at each complementary base position of every template is identical and given by the fraction labeled, f. This implies that the probability of labeled incorporation is independent of sequence context, and, furthermore, that the presence of adjacent fluorescent labels upstream does not affect the probability of labeled incorporation downstream. Second, each labeled dye molecule contributes the same average amount of fluorescence intensity to the image so that the total measured fluorescence intensity is proportional to the number of labeled bases incorporated in a homopolymer stretch. This ignores the effects of quenching.

In any practical experimental implementation of nSBS, several important factors have to be taken into consideration. These include:

(1) The probability of misincorporation by the DNA polymerase. Misincorporation is the erroneous addition of a nucleotide which does not form a normal Watson-Crick base pair to the base on the template.
(2) The probability of incomplete extension from the priming 3' hydroxyl group. Incomplete extension is the failure to add a nucleotide that is complimentary to the base on the template during a given nucleotide flow.
(3) Detection noise and fluorescence intensity variation of the dye molecules. These simulations take these factors into account to determine their potential impact on read lengths and error rates.

Intensity Distribution and Determination of Homopolymer Lengths

A theoretical limitation in the accuracy of calling homopolymer bases arises due to the random distribution of the number of labeled nucleotides incorporated during each nucleotide flow. Let N be the number of copies of our DNA template and L be the length of the homopolymer of a given base type to be called during the next nucleotide flow of the complementary base type. If the homopolymer stretch on every template is completely extended there will be a total of N·L nucleotides incorporated. If each nucleotide has a probability, f, of being fluorescently labeled, then the total number of labeled nucleotides incorporated during a single nucleotide flow is a random variable that follows the binomial distribution. On average there will be L·N·f labeled nucleotides incorporated. The probability of there being exactly K labeled nucleotides incorporated is given by:

$$p(K; N \cdot L, f) = \binom{N \cdot L}{K} f^K (1-f)^{N \cdot L - K} \quad (1.1)$$

The probability distribution for homopolymer lengths varying from 1 through 20 are shown in FIG. 2D with 1,000 templates and 10% fraction labeled. Any overlap between these distributions represents the theoretical error in distinguishing homopolymer lengths. These errors can be minimized by using the intersection between the adjacent probability distributions as cutoff values. Using the assumption that each fluorophore contributes the same amount of fluorescence intensity we normalize this intensity contribution from a single dye to 1. Then the fluorescence intensity exactly determines the number of fluorescent molecules incorporated. For example, in the inset of FIG. 2D the shading in blue (left) represents the error rate for a single deletion when calling a homopolymer of length 10. Similarly, the shading in red (right) represents the error rate for a single insertion when calling a homopolymer of length 10. Interestingly, the probability of a single insertion error will always be slightly larger than the probability of a single deletion (red area>blue area). The overlap is minimal for short homopolymers less than 4 bases and gradually increases with significant overlap between 19-base homopolymers and 20-base homopolymers. There is even a small amount of overlap between 18-base homopolymers and 20-base homopolymers that would result in two deletions or insertions. Since the binomial probability distribution is a discrete distribution (i.e. $p(x)\{x \notin \sqcup\}=0$, where $\sqcup$ is the set of natural numbers) we can use fractional cutoff values to eliminate ambiguities when performing the theoretical error calculations in the next section.

Theoretical Error Calculations

For a given homopolymer length, L, the expected raw error rate of reads for an ideal base caller can be calculated. The majority of the error comes from incorrectly undercalling or overcalling the homopolymer stretch by a single base. To express this error in terms of raw error rate for a read, one can consider the number of errors per base read. In this case it would be $1/(L-1)$ and $1/(L+1)$ respectively. Clearly, an off-by-one error in a 20-base homopolymer would contribute much less to the raw error rate of a read than an off-by-one error in a 5-base homopolymer. Furthermore, if our homopolymer is sufficiently long ($L>=5$) we can ignore the contribution from a missed call ($L=0$), which would otherwise result in an undefined raw error rate (i.e. divided by zero). The total raw error rate then becomes the error from deletions plus the error from insertions:

$$\sum_{i=1}^{L-1} \frac{L-i}{i} \left[ \sum_{K=c(i-1,i;N,f)}^{c(i,i+1;N,f)} p(K; N \cdot L, f) \right] + \sum_{i=L+1}^{\infty} \frac{i-L}{i} \left[ \sum_{K=c(i-1,i;N,f)}^{c(i,i+1;N,f)} p(K; N \cdot L, f) \right]$$  (1.2)

where c(i, i+1; N, f) is the cutoff value (intersection) between the length i and length i+1 homopolymer distributions given N templates and a fraction labeled f. Since a length $L=0$ homopolymer has zero probability of any nucleotide incorporations we define $$c(0,1;N,f)=0.5$$  (1.3)

The bracketed terms in Equation 1.2 can be evaluated using the binomial cumulative distribution function. In evaluating the error rate, we limited the maximum number of insertions to 3 times the length of the homopolymer (e.g. 15 insertions with L=5), which did not affect the precision of the calculation.

Monte Carlo Simulations

Base Calling Algorithms.

Two different base callers in the Monte Carlo Simulations of nSBS were used to determine the bounds on the error rates that can be expected. Both base callers used the theoretical distributions from Equation 1.1. The first base caller is called the simple base caller. It makes use of a priori knowledge of the rate of misincorporation (e.g. 0.2%). Using this information, it can adjust the distribution of homopolymer intensities from Equation 1.1 based on an estimation of the number of viable templates remaining (i.e. those without a misincorporation). Given the misincorporation rate $p_m$, the number of total nucleotide flows F, and the initial number of templates $N_0$, the estimated number of remaining templates is:

$$N=N_0(1-p_m)^F$$  (1.4)

Although the estimation will be accurate, it is not perfect due to the randomness introduced into the simulation. Furthermore, this naïve approach cannot make adjustments for the spurious signal generated by unsynchronized templates resulting from incomplete extension.

The second base caller is called the ideal base caller. It is more sophisticated because it has ideal knowledge of the exact positions of every template throughout the course of a simulation experiment. Therefore, it can accurately adjust for the number of templates lost from misincorporation as well as subtract out any signal from unsynchronized templates. It cannot, however, account for error arising from added noise or dye variation. Furthermore, the ideal base caller is susceptible to error resulting from the overlap in the underlying distributions of homopolymer intensities. A real base caller, regardless of how good its error correction ability is, would perform worse than the ideal base caller.

Although the theoretical cutoff value between a non-call ($L=0$) and a 1-base homopolymer is given by Equation 1.3, the presence of misincorporations and incomplete extensions makes this cutoff value suboptimal since the presence of even a single fluorophore, excluding noise, would eliminate the possibility of a non-call. A heuristic cutoff value is selected that makes the error rate for insertion equal to the error rate for deletion when calling a 1-base homopolymer. This makes the lower and upper cutoff values symmetric about the average number of labeled nucleotides for a 1-base homopolymer (N·f) and can be expressed as follows $$c(0,1;N,f)=2 \cdot N \cdot f - c(1,2;N,f)$$  1.5

General Method.

Simulations of nSBS experiments were performed using the following basic input parameters:

S: Sequence
N: Number of template copies
f: Fraction labeled
R: Read length

S is a random segment of DNA selected from the reference sequence of Chromosome 22 of the Human Genome, March 2006 (hg18) NCBI Build 36.1. Gap sequences, represented by 'N' or 'n', were removed. The length of the DNA sequences selected was sufficiently large so that the desired read length R would be achieved even if a significant number of deletion errors were made. For each DNA template of the N total copies, an index into the sequence S is used to keep track of the position for the next nucleotide addition. The simulation is carried out by performing successive (cyclic) nucleotide flows. As nucleotides are incorporated into each template, the index into the sequence S for that template increases.

Each nucleotide added has a random chance f of being fluorescently labeled. This randomness is achieved using uniformly distributed pseudo-random numbers between 0 and 1. A value below f would indicate insertion of a labeled nucleotide while a value above f would be insertion of a natural nucleotide. After each flow, the total number of fluorescently incorporated nucleotides for all templates is calculated and passed to a base calling algorithm to determine the homopolymer length to add to the read. By comparing the called homopolymer length to the actual homopolymer length in the DNA sequence, insertion and deletion errors can be determined and tracked for each position in a read. Substitutions are not considered because they would not represent an actual error in the sequencing process and, furthermore, can only be determined by alignment of the finished read to the reference sequence. Insertion errors are counted at each of the positions in the read corresponding to the insertion. All deletions errors for a given homopolymer call are counted at the read position immediately following that homopolymer. This biases the error towards the end of reads but is not noticeable in the average error rate after the first few base positions.

All simulations assumed 100% cleavage of fluorescent labels prior to each nucleotide flow. Since the probability of a fluorescent label remaining after multiple cycles of cleavage is low, this approximation is reasonable. After R bases have been called, the simulation terminates and the errors are stored. Simulations were performed 10,000 times for each set of input parameters. Error rates were calculated at each base position by adding up the total number of errors for that position across all the simulations and then dividing by 10,000. A sample size of 10,000 provided sufficient averaging for comparison of error rates for different input parameters.

Misincorporation.

A misincorporation can occur either during the flow of a noncomplimentary base or at the end of a complimentary base flow once a homopolymer has been synthesized and a noncomplimentary base is reached. The input parameter is the misincorporation rate $p_m$, representing the probability that a template will have a misincorporated base during a nucleotide flow. Different misincorporation rates for different mismatched base pairs can be used in our simulations. However, for simplicity, an identical value was assigned for all mismatches, i.e., a value of either 0.2% or 0.1% (see, e.g., Margulies et al. (2005) Nature 437, 376-80; Mashayekhi & Ronaghi (2007) Anal Biochem 363, 275-87; Mitra et al. (2003) Anal Biochem 320, 55-65). A misincorporated base had the same probability, f, of being labeled as a correctly incorporated base. Since the rate of extension off a misincorporation is practically zero, templates having a misincorporation were marked and no further nucleotide additions were allowed.

Figure 8:
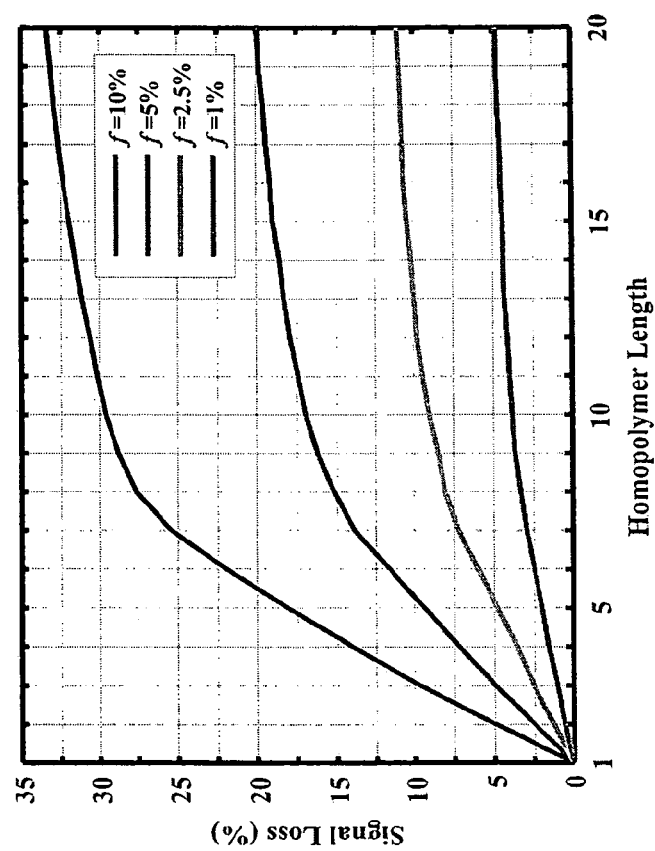
FIG. 8 shows potential signal loss. The percentage of fluorescence labels that would be lost if the minimum spacing required between labeled nucleotides in a homopolymer stretch is 6 bases. Calculated results are shown for homopolymers of length 1 to 20 bases and fractions labeled of 1%, 2.5%, 5% and 10%.

Ideally, the effect of upstream labeled nucleotide on further incorporation of labeled nucleotides downstream is minimized. In general, most DNA polymerases binds to about 12 bases on the DNA template with the 3'-OH priming site and active polymerization site in the middle of that 12-base stretch. In general, a DNA polymerase will have an increased affinity for native nucleotide incorporation over labeled nucleotide incorporation in the presence of upstream labeled nucleotides due to kinetics. Therefore, it is reasonable to assume that the likelihood of incorporating a natural nucleotide will be much greater for any templates that have already had one labeled nucleotide incorporated within 6 bases upstream of the active site. This could result in a lower measured signal than expected. For example, if 5% fraction labeled is used and the homopolymer length is 10, on average, there will be up to 17% less labeled nucleotide incorporations than expected. That percentage will increase more for longer homopolymer stretches and higher % labeled nucleotides (FIG. 8). Depending on the number of templates used, this could potentially contribute a significant amount to sequencing error if not corrected for in the base caller. Since the underlying distribution of homopolymer intensities would vary in a predictable fashion, the base caller can be adjusted to account for these interactions.

Incomplete Extension.

Incomplete extension can occur when DNA polymerase does not bind to a template or the DNA polymerase fails to incorporate a complimentary nucleotide. The latter case could be due to kinetics (e.g., DNA synthesis does not occur on a small population of the templates), accessibility issues (e.g., no diffusion of a complementary nucleotide into the active site of the polymerase) or mechanical hindrance (e.g., the physical entanglement of the DNA template or polymerase leading to the arrest of the activity of the polymerase).

The input parameter is the probability of incomplete extension $p_i$ for each template having a base complimentary to the current nucleotide flow. For each of these templates, a pseudo-random number from a uniform distribution between 0 and 1 was assigned. A value above $p_i$ will have complete complimentary extension for the given template while a value below $p_i$ will have no complimentary bases added. Based on experimental results reported for pyrosequencing and FISSEQ, a value of either 0.2% or 0.1% was used. In the case of complete complimentary extension, misincorporation is still possible at the end of the homopolymer stretch. As with misincorporation, a lack of complete polymerization during one nucleotide flow does not preclude a template from complimentary polymerization in subsequent nucleotide flows. In the case of an incomplete extension, the index (indicating the next position for incorporation) for each template will not increase during the current complimentary flow, but may increase in later flows. This will result in an unsynchronized template, which will contribute to the total observed fluorescence signal and obfuscate base calling.

Effect of Measurement Noise and Dye Fluorescence Intensity Variation.

There are two additional sources of sequencing error. The first source arises from the random distribution in the number of photons emitted from each fluorophore during the exposure time for fluorescent imaging. This could arise due to fluorescence anisotropy, blinking, and photobleaching. If the exposure time is long compared to the fluorescence lifetime then we can approximate this distribution with a normal distribution. As before, we set the mean of this distribution for each fluorophore to 1 so that the total fluorescence intensity equals the number of fluorophores incorporated during a flow. The variance can then be determined from another input parameter for our simulation, c.v. (the coefficient of variation for the normal distribution) as follows:

$$\sigma_{dye}^2 = \mu^2 \cdot c.v.^2 = c.v.^2 \quad (1.6)$$

Where $\sigma_{dye}$ and $\mu$ are the standard deviation and the mean value of the fluorescence intensity of a single dye molecule, respectively. Following a given nucleotide flow we will have a certain number of labeled incorporations, T. The total intensity generated from these T fluorophores will be the sum of the intensities generated from each fluorophore. The distribution for this signal will then have mean T and variance given by $$\sigma^2 = T \cdot \sigma_{dye}^2 = T \cdot c.v.^2 \quad (1.7)$$

A c.v. of 50% is selected as a conservative estimate, which is larger than the reported value of 25% (Harris et al. (2008) Science 320, 106-9; Eid et al. (2009) Science 323, 133-8).

The minimization of fluorescence quenching between the fluorescent molecules in a homopolymer stretch is important, as the length of a homopolymer will be linearly proportional to the measured fluorescence intensity. The fluorescence intensity decreases significantly if two or more fluorophores are incorporated in tandem due to quenching. The Förster radius of most organic dye molecules such as fluorescein is on the order of 50 Å, a length of about 15 bases on a double stranded DNA. This is one reason to select a fraction of labeled nucleotides at 10% or less. Dye molecules with less propensity for self-quenching such as the Alexa dyes can be used to alleviate the problem to some degree. A small amount of quenching may still occur, but can be corrected by a base caller that compensates for the lost signal using an empirically determined quenching factor.

A second source of error is detection noise. The source can be the camera or "shot" noise where fluorescent illumination is scattered by the optics and solvent molecules surrounding the templates. This noise is typically quantified by the signal to noise ratio (SNR). The final parameter to the simulation is the initial SNR for detection of a 1-base homopolymer when all templates are synchronized and none has a misincorporation. We call this parameter $SNR_0$ and assume a normal distribution for this noise such that $$SNR_0 = \frac{\mu_{signal}}{\sigma_{noise}} = \frac{N \cdot f}{\sigma_{noise}} \quad (1.8)$$

Where $\mu_{signal}$ and $\sigma_{noise}$ are the measured fluorescence intensity and the standard deviation of the measurement noise, respectively. As the number of templates is reduced due to misincorporation, the mean of the signal will go down while the variance of the signal will stay constant, effectively reducing the SNR. Similarly, if more templates are used, the mean of the signal will be larger while the variance of the signal will stay constant, effectively increasing $SNR_0$. An SNR of 20 was selected for detecting 100 fluorophores (1,000 template copies; 10% of the nucleotides labeled). This is routinely achieved with the following imaging setup: a TIRF (total internal reflection fluorescence microscopy) system based on a Zeiss AxioObserver microscope.

Both of these components are calculated using normally distributed pseudo-random numbers with mean 0 and variance 1. These random numbers are multiplied by the standard deviations from Equations 1.6 and 1.7, respectively, and then added to the total number of labeled incorporations from the nucleotide flow to generate the final fluorescence intensity that is passed to the base caller.

Results

Theoretical Error Calculations

The error rate as a function of template number is shown in FIG. 2E for all combinations of homopolymer lengths of 5, 10, and 20 bases and fractions labeled of 5%, 10%, and 20%. Highlighting where these functions (including L=15) cross the 1% error rate (i.e. produce Q20 bases). Table 1 lists the number of copies of templates required to produce Q20 reads (the number of bases that can be read with 99% accuracy) for the given number of homopolymer lengths. The number increases monotonically with increasing homopolymer length for the curves shown and a fewer number of templates is required for producing Q20 bases when a higher fraction labeled was used, regardless of homopolymer length. FIG. 2E provides a good guideline for the minimum number of templates that should be present when attempting accurate DNA sequencing with a fixed fraction labeled.

TABLE 1

Number of templates required for 99% accuracy.

|  | L = 5 | L = 10 | L = 15 |
| --- | --- | --- | --- |
| f = 5% | 1474 | 2073 | 2376 |
| f = 10% | 693 | 976 | 1127 |
| f = 20% | 309 | 433 | 505 |

Monte Carlo Simulations

Misincorporation.

The results from 6 simulations using different combinations of fraction labeled and number of templates are shown in FIG. 6A. These simulations included a fixed misincorporation rate of 0.2% per nucleotide flow without considering the impact of other experimental factors ($p_i$=0, c.v.=0, and $SNR_0$=∞). The error rate for 5% fraction labeled and 500 templates was significant (>3%) even at the beginning of the reads. Increasing the fraction labeled to 10% while keeping the number of templates fixed resulted in a Q20 read length of 100 bases, although bases at the beginning of the read are no better than Q23 (>0.5% error rate). With 1,000 templates, a Q20 read length between 300 and 350 was achieved with only 10% labeled nucleotides. With 5,000 templates, the Q20 read length is well beyond 500 bases for all fractions labeled (f=5%, 10%). The difference between the simple and ideal base callers is only noticeable at longer read positions, indicating that at the beginning of the reads the simple base caller is able to accurately predict the number of remaining templates.

Incomplete Extension.

The discrepancy between the simple and ideal base callers is much more pronounced in the case with incomplete extensions. Shown in FIG. 6B are the results from the simulations with the same 6 combinations of fraction labeled and number of templates. For these simulations the rate of incomplete extension was 0.2% and the impact of other experimental factors was not considered ($p_m$=0, c.v.=0, and $SNR_0$=∞). For the ideal base caller, the results are almost identical to the case with only misincorporation, although the case with only incomplete extension performs slightly better. This is because a misincorporation can occur at every nucleotide flow while an incomplete extension can only occur during complimentary flows. That is, more templates are lost (e.g., unsynchronized) in the case with misincorporations compared to the number of unsynchronized templates in the case with incomplete extensions. In both cases, the ideal base caller can accurately adjust for the lost or unsychronized template to make a correct call. The simple base caller, however, can only adjust for misincorporations that result in lost templates. It cannot subtract out spurious signal from unsynchronized templates. Once the amount of signal from unsynchronized templates overpowers the true signal, errors start accumulating. The simple base caller is unable to achieve a Q20 read length over 100 bases in any of the 6 cases considered. FIG. 6B highlights the importance of the base calling algorithm in the presence of incomplete extension.

Effect of Measurement Noise and Dye Fluorescence Intensity Variation.

Figure 7:
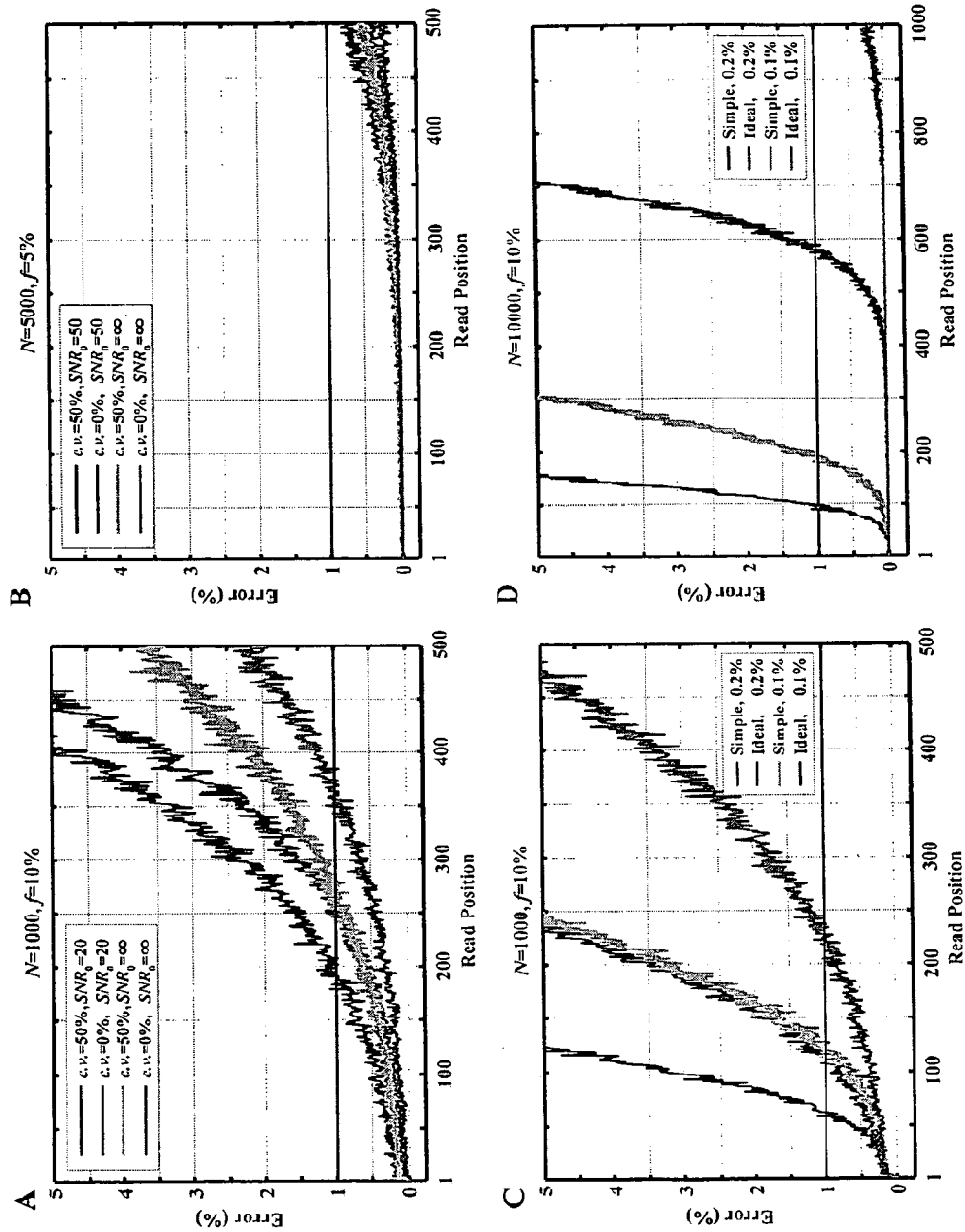
FIG. 7 shows the combined effects of experimental factors on read error.

The effect of measurement noise and dye fluorescence intensity variation on the performance of the ideal base caller is shown in FIG. 7A and FIG. 7B. A misincorporation rate of 0.2% was used for these simulations. The impact of incomplete extensions is not considered. The coefficient of variance in single dye intensity was fixed at 50%. The SNR was fixed at 20 for the detection of 100 fluorophores. This resulted in an initial SNR of 20 for 1,000 templates and 10% labeled nucleotides. With 5,000 templates and 5% nucleotides labeled, the initial SNR increased to 50. The effect of dye fluorescence intensity variation and measurement noise are shown individually and combined. With 1,000 templates and 10% nucleotides labeled there is a significant drop in the Q20 read length from 350 to 250 in the presence of 50% dye fluorescence intensity variation alone. The drop in Q20 read length in the presence of measurement noise alone was almost identical, although the shift is more dramatic for base positions with error rates higher than Q20. This indicated that measurement noise had a larger impact on error rates than dye fluorescence intensity variation when there were 1,000 templates and the fraction labeled was 10%. The combined effect of both dye fluorescence intensity variation and measurement noise drops the Q20 read length even further to 200 bases. When the number of templates is increased to 5,000 and the fraction labeled is dropped to 5%, the error rates drop significantly as expected. In this case, these two sources of sequencing error have a much smaller effect on error rate for read positions less than 500. This indicates that deterioration in Q20 read lengths due to these factors can be mitigated by increasing the number of templates.

Short Read Lengths

Using only 1,000 templates and 10% fraction labeled, shorter read lengths may be achieved with high accuracy. Shown in FIG. 7C is the result of simulations of two different experimental scenarios. Both scenarios have the same amount of signal variation added (c.v.=50% and $SNR_0$=20). The first scenario has a misincorporation rate of 0.2% and an incomplete extension rate of 0.2%, while the second scenario has only 0.1% each. While the first scenario results in a Q20 read length between 75 and 100 bases, the second scenario extends the Q20 read length to between 150 and 200 bases.

Long Read Lengths

The feasibility of read lengths over 500 bases in a practical experimental implementation of nSBS is demonstrated in FIG. 7D. This is achieved by increasing the number of templates to 10,000 while using 10% fraction labeled. We consider two scenarios where the same amount of signal variation was introduced into the simulations (c.v.=50% and $SNR_0$=200). In the first scenario, we consider an experiment which has both a 0.2% misincorporation rate and a 0.2% incomplete extension rate. The second case has more favorable experimental parameters with only a 0.1% misincorporation rate and a 0.1% incomplete extension rate. With a well implemented base caller, Q20 read lengths approaching 600 bases could be achieved even in the presence of 0.2% misincorporation and 0.2% incomplete extension rates. When both the misincorporation rate and the incomplete extension rate are dropped to 0.1% each, a Q20 read length over 1,000 bases can be achieved with a good base caller.

Figure 6:
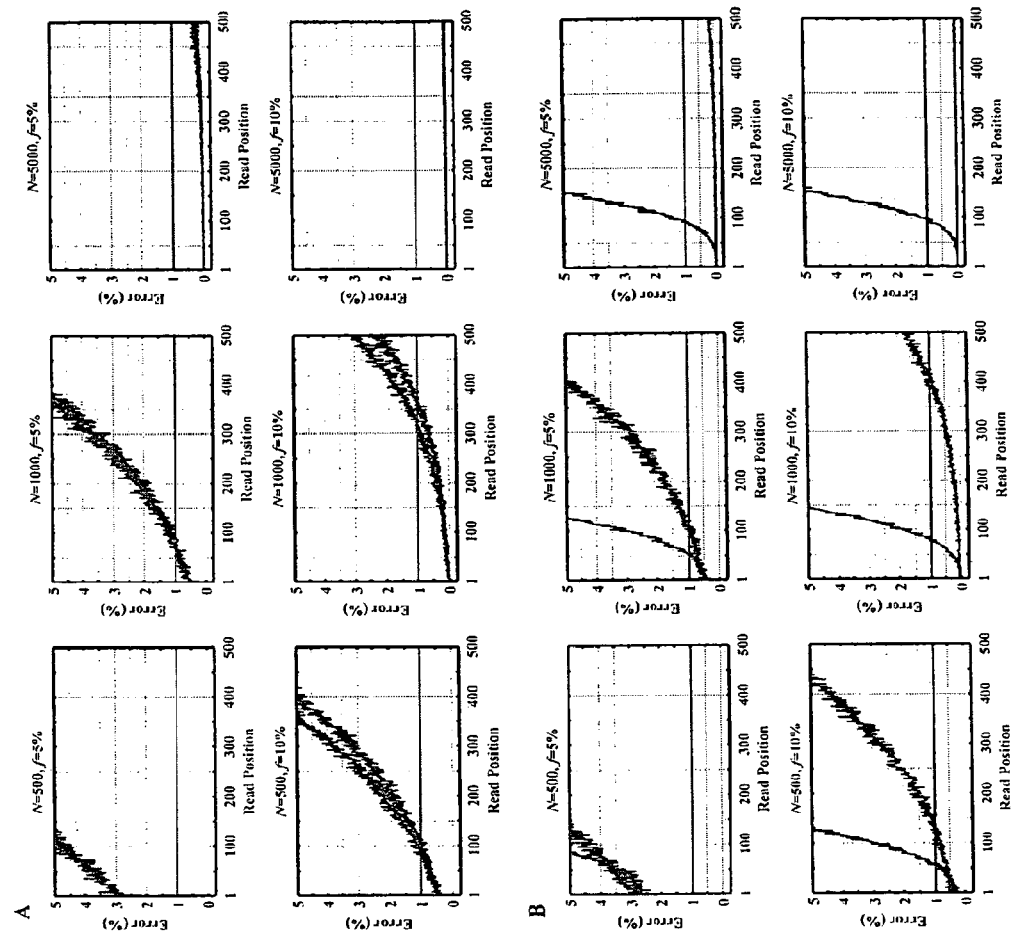
FIG. 6 shows Monte Carlo simulations of nSBS. Reads were performed using either: (A) a misincorporation rate of 0.2% ($p_m$=0.002) or (B) an incomplete extension rate of 0.2% ($p_i$=0.002). All other experimental factors were not considered (c.v.=0 and $SNR_0$=∞). Two different base callers were used: the ideal base caller (green) and the simple base caller (blue). The number of templates (N) was either 500 (column 1), 1,000 (column 2) or 5,000 (column 3). The fraction labeled (f) was either 5% (first rows) or 10% (second rows). The red line indicates Q20 bases (the number of bases that can be obtained with a 1% error rate).

Ultimately, the experimental conditions for sequencing can be optimized such that the probability of incorporating a labeled nucleotide at each base is approximately identical and the measured fluorescent signal after a nucleotide flow will be linearly proportional to the number of bases in a homopolymer stretch. Using the methods disclosed herein, variability between nucleotide flows can be minimized because the fluorescent labels will be removed after each cycle, regenerating nearly natural DNA. As can be seen in FIG. 6, much longer read lengths can be obtained by increasing the fraction labeled. For example, with 1,000 copies of a template, a Q20 read length is increased from about 75 bases to more than 300 bases by increasing the fraction labeled from 5% to 10% (see FIG. 6B). This may not be desirable because the density of incorporated labels will be too high, resulting in more fluorescence quenching and interference with DNA synthesis by the DNA polymerase. Surprisingly, a Q20 read length of more than 1,000 bases can be achieved with only 10% labeled nucleotides and 10,000 copies of a template (FIG. 7D), even if all the potential sources of error (misincorporation, incomplete extension, signal variation and detection noise) are considered.

What is claimed is:

1. A method of determining a target DNA sequence, said method comprising:
   a) hybridizing a plurality of polynucleotides that comprise the target DNA sequence with a primer to form a plurality of hybridized templates;
   b) contacting the plurality of hybridized templates with i) a DNA polymerase and ii) a first single nucleotide solution, wherein the single nucleotide solution comprises non-terminating, labeled and non-labeled nucleotides, and wherein said percentage of labeled nucleotides incorporated by the DNA polymerase is 20% or less of the total number of nucleotides incorporated, under conditions to allow target DNA-dependent extension from the primer if the appropriate single nucleotide is present;
   c) washing to remove unincorporated nucleotides; and
   d) detecting the presence or absence of an incorporated, labeled nucleotide among the plurality of hybridized templates, wherein, when the presence of an incorporated, labeled nucleotide is detected, the presence and size, or absence of a stretch of more than one base of the same type in tandem is also detected,
   thereby determining the target DNA sequence.

2. The method of claim 1, further comprising: e) until a signal is detected, repeating steps b)-d) with a second, third, and fourth single nucleotide solution; and f) optionally cleaving the label from the incorporated labeled nucleotide; and repeating steps b)-f).

3. The method of claim 1, further comprising: e) repeating steps b)-d) with a second, third, and fourth single nucleotide solution; and f) optionally cleaving the label from the incorporated labeled nucleotide; and repeating steps b)-f).

4. The method according to claim 1, wherein the plurality of hybridized templates are attached to a solid support.

5. The method of claim 4, wherein the solid support comprises more than one distinct area, wherein the plurality of hybridized templates are attached to the solid support in the more than one distinct area.

6. The method of claim 5, wherein the target DNA sequence in each of the plurality of hybridized templates in each distinct area on the solid support is the same.

7. The method of claim 5, wherein the target DNA sequence in each of the plurality of hybridized templates is different between each distinct area on the solid support.

8. The method of claim 5, wherein the method of determining the target DNA sequence is performed in parallel in the more than one distinct areas.

9. The method of claim 1, wherein the percentage of labeled nucleotide incorporated is 1-10% of the total number of nucleotides incorporated.

10. The method of claim 9, wherein the percentage of labeled nucleotide incorporated is 5-10% of the total number of nucleotides incorporated.

11. The method of claim 1, wherein the labeled nucleotides comprise a cleavable linker.

12. The method of claim 1, wherein the target DNA sequence is from genomic DNA.

13. The method of claim 1, wherein the polynucleotide comprising the target DNA sequence is amplified before step a).

14. The method of claim 1, wherein the target DNA sequence is at least 1000 nucleotides in length.

15. The method of claim 1, wherein the primer comprises a hairpin primer that is ligated to the plurality of polynucleotides comprising the target DNA sequence.

16. The method of claim 15, wherein the method further comprises paired end sequencing.

* * * * *